(12) United States Patent
Chambers et al.

(10) Patent No.: US 9,399,647 B2
(45) Date of Patent: Jul. 26, 2016

(54) PROTEASOME ACTIVITY MODULATING COMPOUNDS

(71) Applicant: Proteostasis Therapeutics, Inc., Cambridge, MA (US)

(72) Inventors: Robert J. Chambers, Charlestown, MA (US); Megan Foley, Cambridge, MA (US); Bradley Tait, Malden, MA (US)

(73) Assignee: Proteostasis Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/333,820

(22) Filed: Jul. 17, 2014

(65) Prior Publication Data

US 2015/0166565 A1 Jun. 18, 2015

Related U.S. Application Data

(63) Continuation of application No. PCT/US2013/022921, filed on Jan. 24, 2013.

(60) Provisional application No. 61/590,605, filed on Jan. 25, 2012, provisional application No. 61/681,410, filed on Aug. 9, 2012, provisional application No. 61/739,069, filed on Dec. 19, 2012.

(51) Int. Cl.
*C07D 487/04* (2006.01)
*C07D 495/04* (2006.01)

(52) U.S. Cl.
CPC .................................... *C07D 495/04* (2013.01)

(58) Field of Classification Search
CPC ....................................................... C07D 487/04
See application file for complete search history.

(56) References Cited

U.S. PATENT DOCUMENTS

| | | | |
|---|---|---|---|
| 3,577,420 | A | 5/1971 | Hess et al. |
| 6,482,948 | B1 | 11/2002 | Yamada et al. |
| 6,849,638 | B2 | 2/2005 | Stolle et al. |
| 8,933,087 | B2 | 1/2015 | Finley et al. |
| 2003/0119829 | A1 | 6/2003 | Stolle et al. |
| 2004/0063943 | A1 | 4/2004 | Eggenweiler et al. |
| 2004/0077664 | A1 | 4/2004 | Eggenweiler et al. |
| 2004/0242595 | A1 | 12/2004 | Eggenweiler et al. |
| 2007/0155777 | A1 | 7/2007 | Burkitt et al. |
| 2010/0120805 | A1 | 5/2010 | Hsieh et al. |
| 2010/0227853 | A1 | 9/2010 | Hoffman et al. |
| 2012/0022046 | A1 | 1/2012 | Byrd et al. |
| 2012/0065200 | A1 | 3/2012 | Barbosa et al. |
| 2013/0045992 | A1 | 2/2013 | Finley et al. |
| 2015/0166567 | A1 | 6/2015 | Chambers et al. |
| 2016/0039839 | A1 | 2/2016 | Finley et al. |

FOREIGN PATENT DOCUMENTS

| | | |
|---|---|---|
| DE | 237 663 A1 | 7/1986 |
| DE | 245666 A1 | 5/1987 |
| DE | 10104097 A1 | 8/2002 |
| JP | 01-313480 A | 12/1989 |
| JP | 2002-105082 A | 4/2002 |
| WO | 98/29397 A1 | 7/1998 |
| WO | 0066585 A1 | 11/2000 |
| WO | 02088138 A1 | 11/2002 |
| WO | 03037898 A1 | 5/2003 |
| WO | 2004065391 A1 | 8/2004 |
| WO | 2006/034511 A1 | 3/2006 |
| WO | 2007061764 A2 | 5/2007 |
| WO | 2009/029473 A1 | 3/2009 |
| WO | 2009/033581 A1 | 3/2009 |
| WO | 2009/086303 A2 | 7/2009 |
| WO | 2010006032 A1 | 1/2010 |
| WO | 2011/029054 A1 | 3/2011 |
| WO | 2011/094545 A2 | 8/2011 |
| WO | 2012/012712 A2 | 1/2012 |
| WO | 2012062044 A1 | 5/2012 |
| WO | 2012097013 A1 | 7/2012 |
| WO | 2013106535 A1 | 7/2013 |

OTHER PUBLICATIONS

CAS Registry No. 305796-86-5, STN Entry Date Dec. 1, 2000; 5H-Pyrimido[4,5-b]indole-2-carboxylic acid, 4- (dipropylamino)-6,7,8,9-tetrahydro-9-(2,4,6-trimethylphenyl)-, ethyl ester.
CAS Registry No. 305796-87-6, STN Entry Date Dec. 1, 2000; 5H-Pyrimido[4,5-b]indole-2-methanamine,4- (dipropylamino)-6,7,8,9-tetrahydro-9-(2,4,6-trimethylphenyl)-.
CAS Registry No. 305796-88-7, STN Entry Date Dec. 1, 2000; 5H-Pyrimido[4,5-b]indole-2-carboxamide, 4- (dipropylamino)-6,7,8,9-tetrahydro-9-(2,4,6-trimethylphenyl)-.
Iinformation Disclosure Statement Under Rule 56, Sep. 24, 2015.
Sleebs, B. E., et al., "Identification of 5,6-substituted 4 aminothieno[2,3-d]pyrimidines as LIMK1inhibitors", Bioroganic & Medicinal Chemistry Letters, 2011, 21, 5992-5994.
Modica, M., et al., "Synthesis and binding properties of novel selective 5-HT3 receptor ligands", Bioroganic & Medicinal Chemistry, 2004, 12, 3891-3901.
Rosowsky, A., et al., "2,4-Diaminothieno[2,3-d]pyrimidines as antifolates and antimalarials. 1. Synthesis of 2,4-diamino-5,6,7,8-tetrahydrothianaphtheno[2,3-d]pyrimidines and related compounds", J. Med. Chem., 1973, 16(3), 185-188.
Card, G. L., et al., "A family of phosphodiesterase inhibitors discovered by cocrystallography and scaffold-based drug design," Nature Biotechnology, 23(2): 201-207 (2005).
Christian, F., et al., "p62 (SQSTM1) and cyclic AMP phosphodiesterase-4A4 (PDE4A4) locate to a novel, reversible protein aggregate with links to autophagy and proteasome degradation pathways," Cellular Signalling, 22: 1576-1596 (2010).
Lee, B.-H., et al., "Enhancement of Proteasome Activity by a Small-Molecule Inhibitor of Usp14," Nature, 467(7312): 179-184 (2010).
Ma, T., et al., "Membrane Transport Structure Function and Biogenesis: High-affinity Activators of Cystic Fibrosis Transmembrane Conductance Regulator (CFTR) Chloride Conductance Identified by High-throughput Screening," J. Bioi. Chern., 277: 37235-37241 (2002).
CAS Registry No. 1055410-87-1, STN Entry Date Sep. 30, 2008; [1]Benzothieno[2,3-d]pyrimidin-4-amine, N-cyclohexyl-5,6,7,8-tetrahydro-N-(1-methylethyl)-.
Finley, et al., co-pending U.S. Appl. No. 14/572,927, filed Dec. 17, 2014.

(Continued)

*Primary Examiner* — Bruck Kifle
(74) *Attorney, Agent, or Firm* — Elmore Patent Law Group, P.C.; Mahreen Chaudhry Hoda; Carolyn S. Elmore, Esq.

(57) ABSTRACT

The present invention is directed to compounds having the Formula (I), (Ia) or (Ib), compositions thereof and methods for the treatment of a condition associated with a dysfunction in proteostasis.

11 Claims, No Drawings

(56) References Cited

OTHER PUBLICATIONS

Pédeboscq, S., et al., "Synthesis and study of antiproliferative activity of novel thienopyrimidines on glioblastoma cells," European Journal of Medicinal Chemistry, 45: 2473-2479 (2010).
Briel, D., et al., "Thieno[2,3-d]pyrimidine als Glutamatantagonisten," Pharmazie, 63: 823-826 (2008).
CAS Registry No. 1276345-40-4, STN Entry Date Apr. 7, 2011; 2-[propyl(5,6,7,8-tetrahydropyrido[4',3':4,5]thieno[2,3-d]pyrimidin-4-yl)amino]-cyclohexanol.
CAS Registry No. 382648-55-7, STN Entry Date Jan. 14, 2002; 5,8-dihydro-6,6-dimethyl-6H-pyrano[4',3':4,5]furo[2,3-d]pyrimidin-4-amine.
Hu, et al., "Structure and mechanisms of the proteasome-associated deubiquitinating enzyme USP14," The EMBO Journal, 24: 3747-3756 (2005).
Banker, G.S. et al., "Modern Pharmaceutics, 3ed.," Marcel Dekker, New York, 1996, p. 596.
Wolff, M. E., "Burger's Medicinal Chemistry and Drug Discovery, 5ed., vol. 1," John Wiley & Sons, 1995, pp. 975-977.
Pech, R. et al., "Ueber Thienoverbindungen 11. Mitteilung: Darstellung 4-Aminosubstituierter Thieno not 2,3-D 3/4 Pyrimidin-2-Ylcarbonsaeurederivate 3/4", Die Pharmazie, Govi Verlag Pharmazeutischer Verlag GMBH; Eschborn, DE, vol. 46, No. 6: 422-423, Jan. 1, 1991.
Pech, et al., "New thieno compounds. Part 12. Preparation of 4-amino substituted thieno [2, 3-d] pyrimidin-2-ylacetic acid derivatives," Die Pharmazie, Govi Verlag Pharmazeutischer Verlag GMBH, Eschborn, DE, vol. 47, No. 1: 20-21, Jan. 1, 1992.
Modica, M. N., et al., "Synthesis and Receptor Binding of New Thieno[2,3-d]-pyrimidines as Selective Ligands of 5-HT3Receptors," Archiv Der Pharmazie, vol. 341, No. 6: 333-345, Jun. 5, 2008.
Aly, A. S., et al., "The synthesis of some new derivatives derived from 1,2,3,4.tetrahydrocycloheptено[4,5]thieno-[2,3-d]pyrimidine," Phosphorus, Sulfur and Silicon and the Related Elements, vol. 182, No. 1: 35-36, Jan. 1, 2007.
Van Der Horst, E., et al., "Supporting Information Substructure-Based Virtual Screening for Adenosine A 2A Receptor Ligands," CHEMMEDCHEM, vol. 6, No. 12: S1-S100, Oct. 21, 2011.
Hussein, et al., "Novel Synthesis of fused pyrazolopyrimidines and C-nucleosides of theinopyrimidone with expected antimicrobial activity," Egyptian Journal of Chemistry, National Information and Documentation Centre (NIDOC), Cairo; EG, vol. 53, No. 4: 527-540, Jan. 1, 2010.
Abu-Zied, et al., "Synthesis and reactions of some novel azolothienopyrimidines and thienopyrimido-as-triazine derivatives," Phosphorus and Sulfur and the Related Elements, Gordon and Breach—Harwood Academic, CH, vol. 182, No. 2: 447-474, Jan. 1, 2007.
Choi, I. K., et al., "Autophagonizer, a novel synthetic small molecule, induces autophagic cell death," Biochemical and Biophysical Research Communications, Academic Press Inc. Orlando, FL, US, vol. 393, No. 4: 849-854, Mar. 19, 2010.
Bhaskar, et al., "Synthesis and Antibacterial Evaluation of Some 4-Substituted 5,6,7.8-Tetrahydro[1 ]Benzothieno [2,3-d]Pyrimidine Derivatives," Indian Journal of Heterocyclic Chemistry, 16:309-310 (2007).
Bohm, et al., "Mitteilung: Basisch substitulerte Thieno[2,3-d]pyrimidine," Pharmazie, 41 (1):23-25 (1986).
Konno, et al., "Synthesis of Thieno[2,3-d]pyrimidine Derivatives and Their Antifungal Activities," Yakuqaku Zasshi (Journal of the Pharmaceutical Society of Japan), 109(7):464-473 (1989).
Ming et al., "Heterocondensed Pyridines by Cycloaddition-Extrusion Sequence of Bi- and Tricyclic 1,3-Oxzainones with N,N-Diethyl-1-propynylamine," Chemische Berichte, 120(8):1427-1431 (1987).
Univeristy of Florida. Office of Technology Licensing. "Soluble, Toll-Like Receptor Decoys for Treating Neurodegenerative Diseases." © 2014. Available from: < http://technologylicensing.research.ufl.edu/technologies/14631_soluble-toll-like-receptor-decoys-for-treating-neurodegenerative-diseaes >.

PROTEASOME ACTIVITY MODULATING COMPOUNDS

RELATED APPLICATIONS

This application is a continuation of International Application No. PCT/US2013/022921, which designated the United States and was filed on Jan. 24, 2013, published in English, which claims the benefit of U.S. Provisional Application No. 61/590,605, filed Jan. 25, 2012, U.S. Provisional Application No. 61/681,410, filed Aug. 9, 2012 and U.S. Provisional Application No. 61/739,069, filed Dec. 19, 2012. The entire teachings of the above applications are incorporated herein by reference.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., Nature 426: 891-894, 2003; Ron et al., Nat Rev Mol Cell Biol 8: 519-529, 2007]. The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., Cell 131: 809-821, 2007]. Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., Nature 426: 905-909, 2003]. Human gain of function diseases are similarly frequently the result of a disruption in protein homeostasis, such as the accumulation of misfolded proteins, leading to protein aggregation [Balch et al. (2008), Science 319: 916-919].

The proteasome is a large protein complex of multiple subunits which acts as a protease to degrade misfolded proteins. Most proteasome substrates are targeted for degradation by the covalent attachment of ubiquitin moieties which are recognized by the proteasome [Lee et al. (2010), Nature 467(7312): 179-184]. Proteins with longer ubiquitin chains tend to have a stronger association with the proteasome than those with smaller chains [Lee et al. (2010); Proctor et al. (2007), BMC Systems Biology 1: 17]. The length of the ubiquitin chains is modulated, in part, by proteasome-associated deubiquitinating enzymes. One such mammalian deubiquitinating enzyme is Usp14 which has been shown to act as an inhibitor of the proteasome [Lee et al. (2010)].

Both proteasome dysfunction and dysfunction in proteostasis have been implicated in a diverse range of diseases including for example, neurodegenerative disease, metabolic diseases, inflammatory diseases, and cancer. In many such diseases and conditions, the proteasome has decreased ability to degrade misfolded or abnormal proteins, leading to the presence of toxic protein aggregates. In addition, the enhancement of proteasome activity can be therapeutic for any disease characterized by deficient proteasome activity, or deficient activity of other components of the ubiquitin-proteasome pathway including, but not limited to, von Hippel-Lindau disease, spinocerebellar ataxia 1, Angelman syndrome, giant axon neuropathy, inclusion body myopathy with Paget disease of bone and frontotemporal dementia (IBMPFD), and others (Lehman, N. L., (2009), Acta Neuropathologica, 118(3), 329-347; Weihl et al., (2007), Neuromuscular Disorders, 17, 87-87). Enhancing proteasome activity is also therapeutic for diseases in which proteasome substrates are involved and contribute to pathology, but which do not satisfy a strict definition of proteinopathies. For example, numerous oncoproteins are proteasome substrates and their ability to promote cancer can potentially be attenuated by enhancing proteasome activity. Therefore, there is a need for compounds and pharmaceutical compositions to treat conditions associated with proteostasis dysfunction and/or that provide therapies based on enhancing proteasome activity.

SUMMARY OF THE INVENTION

The present invention is based, in part, on the discovery that compounds of the invention inhibit Usp14. The present invention is directed to compounds encompassed by the Formulae (I), (Ia) and (Ib), compositions thereof, methods for the treatment of a condition associated with a dysfunction in proteostasis, methods for enhancing proteasome activity and methods for treating cancer or tumor.

In one embodiment, the invention is directed to a compound having the Formula (I):

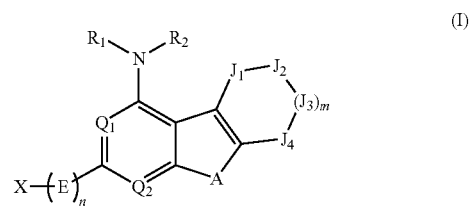

or a pharmaceutically acceptable salt, solvate, clathrate or prodrug thereof; wherein:

$Q_1$ and $Q_2$ are each independently selected from the group consisting of nitrogen and $CR_{6a}$;

A is sulfur, oxygen or $NR_{7a}$;

$R_1$ and $R_2$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or alternatively, $R_1$ and $R_2$ are taken together with the nitrogen atom to which they are attached to form an optionally substituted heterocylic or an optionally substituted heteroaryl;

X is selected from the group consisting of $OR_3$, $C(O)R_3$, $C(O)OR_3$, $OC(O)R_3$, $C(O)NR_aR_b$, $C(O)NR_aS(O)_2R_3$, $S(O)_2NR_aR_b$, $S(O)NR_aR_b$, $NR_aS(O)_2R_3$, CN, $SR_3$, $S(O)R_3$, $S(O)_2R_3$, $P(O)(OR_3)_2$, $NR_aR_b$, $N(R_a)OR_3$, $NR_aC(O)C(O)R_3$, $NR_aC(O)R_3$, $NR_aC(O)NR_aR_b$ and $NR_aS(O)_2NR_aR_b$;

$R_3$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_a$ and $R_b$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; alternatively, $R_a$ and $R_b$ are taken together with the nitrogen atom to which they are attached to form an optionally substituted heterocyclic or an optionally substituted heteroaryl;

E is $C(R_{4a})(R_{4b})$;

each of $J_1$, $J_2$, $J_3$ and $J_4$ is independently $C(R_{5a})(R_{5b})$;

each of $R_{4a}$ and $R_{4b}$ are independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_aR_b$, $C(O)OR_c$, $NO_2$, CN, $C(O)R_c$, $C(O)C(O)R_c$, $C(O)NR_aR_b$, $NR_aC(O)R_c$, $NR_aS(O)_pR_c$, $N(R_a)C(O)OR_c$, $NR_aC(O)C(O)R_c$, $NR_aC(O)NR_aR_b$, $NR_aS(O)_pNR_aR_b$, $S(O)_pR_c$, $S(O)_pNR_aR_b$, $OC(O)OR_c$, and $(C=NR_a)R_c$; alternatively, $R_{4a}$ and $R_{4b}$ can be taken together with the carbon atom to which they are attached to form an optionally substituted optionally substituted $C_3$-$C_{12}$ cycloalkyl, optionally substituted $C_3$-$C_{12}$ cycloalkenyl, optionally substituted heterocyclic, optionally substituted aryl or optionally substituted heteroaryl;

each of $R_{5a}$ and $R_{5b}$ are independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_aR_b$, $C(O)OR_c$, CN, $C(O)R_c$, $C(O)C(O)R_c$, $C(O)NR_aR_b$, $C(O)NR_aS(O)_2R_3$, $NR_aC(O)R_c$, $NR_aS(O)_pR_c$, $N(R_a)C(O)OR_c$, $NR_aC(O)C(O)R_c$, $NR_aC(O)NR_aR_b$, $NR_aS(O)_pNR_aR_b$, $S(O)_pR_c$, $S(O)_pNR_aR_b$, $OC(O)OR_c$, and $(C=NR_a)R_c$; alternatively, geminal $R_{4a}$ and $R_{5b}$ can be taken together with the carbon atom to which they are attached to form a spiro $C_3$-$C_{12}$ cycloalkyl, a spiro $C_3$-$C_{12}$ cycloalkenyl, a spiro heterocyclic, a spiro aryl or spiro heteroaryl, each optionally substituted;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_{6a}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl, halo, $OR_c$, $SR_c$, $NR_aR_b$, $C(O)OR_c$, $NO_2$, CN, $C(O)R_c$, $C(O)C(O)R_c$, $C(O)NR_aR_b$, $NR_aC(O)R_c$, $NR_aS(O)_pR_c$, $N(R_a)C(O)OR_c$, $NR_aC(O)C(O)R_c$, $NR_aC(O)NR_aR_b$, $NR_aS(O)_pNR_aR_b$, $S(O)_pR_c$, $S(O)_pNR_aR_b$, $OC(O)OR_c$, and $(C=NR_a)R_c$;

$R_{7a}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

m and n are each independently selected from the group consisting of 0, 1, 2 and 3; and p is 1 or 2.

In an additional embodiment, the invention is a compound having the Formula (Ia):

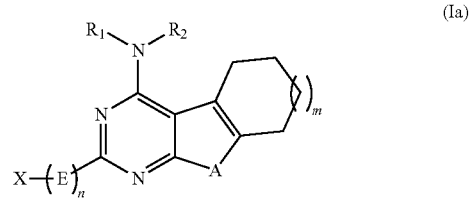

(Ia)

or a pharmaceutically acceptable salt, solvate, clathrate or prodrug thereof; wherein A, $R_1$, $R_2$, E, X, $R_3$, $R_{4a}$, $R_{4b}$, $R_a$, $R_b$, $R_c$, $R_{7a}$, m, n and p are as defined above for Formula (I).

In a further embodiment, the invention is directed to a compound having to Formula (Ib):

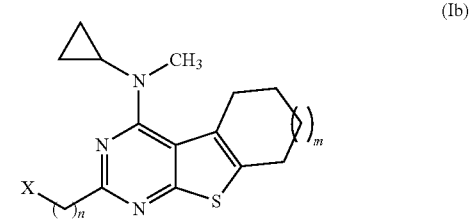

(Ib)

or a pharmaceutically acceptable salt, solvate, clathrate or prodrug thereof; wherein X, $R_3$, $R_a$, $R_b$, m, n and p are as defined above for Formula (I).

In additional embodiments, the invention is directed to a pharmaceutical composition comprising a pharmaceutically acceptable carrier or excipient and a compound of Formulae (I), (Ia) or (Ib), or a pharmaceutically acceptable salt, solvate, clathrate or prodrug thereof.

In an additional aspect, the invention is directed to a method of inhibiting the deubiquitination activity of a Usp14 protein comprising contacting the Usp14 protein with a compound of Formulae (I), (Ia) or (Ib), or a pharmaceutically acceptable salt, solvate, clathrate or prodrug thereof in an amount sufficient to inhibit the deubiquitination activity of the Usp14 protein.

In yet another embodiment, the invention is directed to a method of enhancing protein degradation by a proteasome in a cell comprising contacting the cell with a compound of Formulae (I), (Ia) or (Ib), or a pharmaceutically acceptable salt, solvate, clathrate or prodrug thereof in an amount sufficient to enhance protein degradation by the proteasome.

In additional embodiments, the invention encompasses a method of treating a patient suffering from a condition associated with a dysfunction in proteostasis comprising administering to said patient an effective amount of a compound of Formulae (I), (Ia) or (Ib).

In another aspect, the invention is directed to a method of enhancing proteasome function in a subject in need thereof comprising administering to said subject an effective amount of a compound of Formulae (I), (Ia) or (Ib), or a pharmaceutically acceptable salt, solvate, clathrate or prodrug thereof.

In a further embodiment, the invention is directed to a method for treating a condition characterized by deficient proteasome activity or deficiency of other components of the ubiquitin-proteasome pathway in a subject comprising administering to said subject an effective amount of a compound of Formulae (I), (Ia) or (Ib), or a pharmaceutically acceptable salt, solvate, clathrate or prodrug thereof.

In yet another embodiment, the invention encompasses a method of treating cancer or a tumor in a subject in need thereof comprising administering to said subject an effective amount of a compound of Formulae (I), (Ia) or (Ib), or a pharmaceutically acceptable salt, solvate, clathrate or prodrug thereof.

In a further aspect, the invention is a pharmaceutical composition comprising:
a pharmaceutically acceptable carrier or excipient;
an agent selected from the group consisting of a proteostasis regulator and a pharmacologic chaperone; and
a compound of Formulae (I), (Ia) or (Ib), or a pharmaceutically acceptable salt, solvate, clathrate or prodrug thereof.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

As discussed above, the present invention is directed to compounds of Formulae (I), (Ia) and (Ib), pharmaceutical compositions thereof, methods of use thereof in the treatment of conditions associated with a dysfunction in proteostasis, methods of enhancing proteasome activity and methods for treating cancer or a tumor.

In some aspects, the invention is directed to a compound having the Formula (I); or a pharmaceutically acceptable salt, solvate, clathrate or prodrug thereof.

In certain aspects, the compound has the Formula (I), or is a pharmaceutically acceptable salt, solvate, clathrate or prodrug thereof, wherein A is sulfur.

In certain additional aspects, the compound has the Formula (I), or is a pharmaceutically acceptable salt, solvate, clathrate or prodrug thereof, wherein at least one of $Q_1$ and $Q_2$ is nitrogen.

In additional embodiments, the compound has the Formula (I), or is a pharmaceutically acceptable salt, solvate, clathrate or prodrug thereof, wherein each of $R_{5a}$ and $R_{5b}$ are independently selected from hydrogen and optionally substituted $C_1$-$C_{10}$ alkyl. In yet an additional aspect, $R_{5a}$ and $R_{5b}$ are each independently selected from hydrogen and $C_1$-$C_3$ alkyl.

In a further embodiment, the compound has the Formula (I), or is a pharmaceutically acceptable salt, solvate, clathrate or prodrug thereof, wherein at least one pair of geminal $R_{5a}$ and $R_{5b}$ are taken together with the carbon atom to which they are attached to form a spiro, optionally substituted ring system selected from the group consisting of $C_3$-$C_{12}$ cycloalkyl, $C_3$-$C_{12}$ cycloalkenyl, heterocyclic, aryl or heteroaryl.

In yet another embodiment, the compound has the Formula (I), or is a pharmaceutically acceptable salt, solvate, clathrate or prodrug thereof, wherein $Q_1$ is nitrogen. In yet an additional aspect, the compound has the Formula (I), wherein $Q_2$ is $CR_{6a}$.

In a further aspect, the compound has the Formula (I), wherein $Q_2$ is nitrogen.

In a further aspect, the compound has the Formula (I), or is a pharmaceutically acceptable salt, solvate, clathrate or prodrug thereof, wherein each of $R_{4a}$ and $R_{4b}$ are independently selected from hydrogen and optionally substituted $C_1$-$C_{10}$ alkyl. In another aspect, each of $R_{4a}$ and $R_{4b}$ are independently selected from hydrogen and optionally substituted $C_1$-$C_3$ alkyl.

In yet another aspect, the compound has the Formula (I), or is a pharmaceutically acceptable salt, solvate, clathrate or prodrug thereof, wherein at least one pair of geminal $R_{4a}$ and $R_{4b}$ are taken together with the carbon atom to which they are attached to form an optionally substituted $C_3$-$C_{12}$ cycloalkyl, optionally substituted $C_3$-$C_{12}$ cycloalkenyl, optionally substituted heterocyclic, optionally substituted aryl or an optionally substituted heteroaryl.

In a further embodiment, the compound has the Formula (I), or is a pharmaceutically acceptable salt, solvate, clathrate or prodrug thereof, wherein n is 0, 1 or 2. In yet another aspect, n is 1.

In an additional aspect, the compound has the Formula (I), or is a pharmaceutically acceptable salt, solvate, clathrate or prodrug thereof, wherein $R_1$ and $R_2$ are each independently selected from the group consisting of optionally substituted $C_1$-$C_8$ alkyl, optionally substituted $C_3$-$C_7$ cycloalkyl and optionally substituted heterocyclic. In another aspect, $R_1$ is optionally substituted $C_1$-$C_8$ alkyl and $R_2$ is optionally substituted $C_3$-$C_7$ cycloalkyl or optionally substituted heterocyclic. In yet another embodiment, $R_1$ is optionally substituted $C_1$-$C_4$ alkyl. In a further aspect, $R_2$ is optionally substituted $C_3$-$C_6$ cycloalkyl or optionally substituted heterocyclic. In yet a further embodiment, $R_2$ is optionally substituted cyclopropyl.

In an additional embodiment, the compound has the Formula (I), or is a pharmaceutically acceptable salt, solvate, clathrate or prodrug thereof, wherein X is $OR_3$.

In a further aspect, X is $OR_3$ wherein $R_3$ is hydrogen or optionally substituted $C_1$-$C_{10}$ alkyl.

In a further embodiment, the compound has the Formula (I), wherein X is $C(O)R_3$, $C(O)OR_3$, $C(O)NR_aR_b$, or $C(O)NR_aS(O)_2R_3$. In another aspect, X is $C(O)R_3$ and $R_3$ is optionally substituted $C_1$-$C_{10}$ alkyl. In yet another aspect, X is $C(O)NR_aR_b$, wherein $R_a$ and $R_b$ are each independently hydrogen or optionally substituted $C_1$-$C_{10}$ alkyl; or alternatively, $R_a$ and $R_b$ are taken together with the nitrogen atom to which they are attached to form an optionally substituted heterocyclic or an optionally substituted heteroaryl. In a further aspect, X is $S(O)_2NR_aR_b$. In yet a further aspect, X is $C(O)NR_aS(O)_2R_3$.

In some embodiments, the compound has the Formula (I), or is a pharmaceutically acceptable salt, solvate, clathrate or prodrug thereof, wherein m is 0 or 1. In an additional aspect, m is 1.

In certain aspects, the compound has the Formula (I), or is a pharmaceutically acceptable salt, solvate, clathrate or prodrug thereof, wherein n is 0, 1 or 2. In yet an additional embodiment, n is 1.

In additional embodiments, the compound has the Formula (Ia), or is a pharmaceutically acceptable salt, solvate, clathrate or prodrug thereof.

In yet an additional aspect, the compound has the Formula (Ia), or is a pharmaceutically acceptable salt, solvate, clathrate or prodrug thereof, wherein A is sulfur.

In another embodiment, the compound has the Formula (Ia), or is a pharmaceutically acceptable salt, solvate, clathrate or prodrug thereof, wherein each of $R_{4a}$ and $R_{4b}$ are each independently selected from hydrogen and optionally substituted $C_1$-$C_{10}$ alkyl. In another aspect, each of $R_{4a}$ and $R_{4b}$ are each independently selected from hydrogen and optionally substituted $C_1$-$C_3$ alkyl.

In yet an additional aspect, the compound has the Formula (Ia), or is a pharmaceutically acceptable salt, solvate, clathrate or prodrug thereof, wherein at least one pair of geminal $R_{4a}$ and $R_{4b}$ are taken together with the carbon atom to which they are attached to form an optionally substituted $C_3$-$C_{12}$ cycloalkyl, optionally substituted $C_3$-$C_{12}$ cycloalkenyl, optionally substituted heterocyclic, optionally substituted aryl or an optionally substituted heteroaryl.

In a further embodiment, the compound has the Formula (Ia), or is a pharmaceutically acceptable salt, solvate, clathrate or prodrug thereof, wherein n is 0, 1 or 2. In some embodiments, n is 1.

In an additional aspect, the compound has the Formula (Ia), or is a pharmaceutically acceptable salt, solvate, clathrate or prodrug thereof, wherein $R_1$ and $R_2$ are each independently selected from the group consisting of optionally substituted $C_1$-$C_8$ alkyl, optionally substituted $C_3$-$C_7$ cycloalkyl and optionally substituted heterocyclic. In another aspect, $R_1$ is optionally substituted $C_1$-$C_8$ alkyl and $R_2$ is optionally substituted $C_3$-$C_7$ cycloalkyl or optionally substituted heterocyclic. In yet another embodiment, $R_1$ is optionally substituted $C_1$-$C_4$ alkyl. In a further aspect, $R_2$ is optionally substituted $C_3$-$C_6$ cycloalkyl or optionally substituted heterocyclic. In yet a further embodiment, $R_2$ is optionally substituted cyclopropyl.

In an additional embodiment, the compound has the Formula (Ia), or is a pharmaceutically acceptable salt, solvate, clathrate or prodrug thereof, wherein X is $OR_3$. In a further aspect, X is $OR_3$ wherein $R_3$ is hydrogen or optionally substituted $C_1$-$C_{10}$ alkyl.

In a further embodiment, the compound has the Formula (Ia), or is a pharmaceutically acceptable salt, solvate, clathrate or prodrug thereof, wherein X is $C(O)R_3$, $C(O)OR_3$, $C(O)NR_aR_b$ or $C(O)NR_aS(O)_2R_3$. In another aspect, X is $C(O)R_3$ and $R_3$ is optionally substituted $C_1$-$C_{10}$ alkyl. In yet another aspect, X is $C(O)NR_aR_b$, wherein $R_a$ and $R_b$ are each independently hydrogen or optionally substituted $C_1$-$C_{10}$ alkyl; or alternatively, $R_a$ and $R_b$ are taken together with the nitrogen atom to which they are attached to form an optionally substituted heterocyclic or an optionally substituted heteroaryl. In a further aspect, X is $S(O)_2NR_aR_b$. In yet a further aspect, X is $C(O)NR_aS(O)_2R_3$.

In some embodiments, the compound has the Formula (Ia), or is a pharmaceutically acceptable salt, solvate, clathrate or prodrug thereof, wherein m is 0 or 1. In an additional aspect, m is 1.

In certain aspects, the compound has the Formula (Ia), or is a pharmaceutically acceptable salt, solvate, clathrate or prodrug thereof, wherein n is 0, 1 or 2. In yet an additional embodiment, n is 1.

In additional aspects, the invention is a compound of Formula (Ib); or is a pharmaceutically acceptable salt, solvate, clathrate or prodrug thereof.

In another embodiment, the invention is a compound of Formula (Ib), or is a pharmaceutically acceptable salt, solvate, clathrate or prodrug thereof, wherein X is $C(O)R_3$, $C(O)OR_3$, $C(O)NR_aR_b$, or $C(O)NR_aS(O)_2R_3$. In some embodiments, X is $C(O)R_3$. In additional embodiments, X is $C(O)R_3$, wherein $R_3$ is optionally substituted $C_1$-$C_{10}$ alkyl, optionally substituted $C_3$-$C_{12}$ cycloalkyl, optionally substituted $C_3$-$C_{12}$ cycloalkenyl, optionally substituted heterocyclic, optionally substituted aryl or optionally substituted heteroaryl. In a further embodiment, $R_3$ is optionally substituted $C_1$-$C_{10}$ alkyl.

In an additional aspect, the invention is a compound of Formula (Ib), or is a pharmaceutically acceptable salt, solvate, clathrate or prodrug thereof, wherein X is $C(O)NR_aR_b$. In some embodiments, $R_a$ and $R_b$ are each independently hydrogen or optionally substituted $C_1$-$C_{10}$ alkyl. In additional embodiments, $R_a$ and $R_b$ are taken together with the nitrogen atom to which they are attached to form an optionally substituted heterocyclic or an optionally substituted heteroaryl.

In a further embodiment, the invention is a compound of Formula (Ib), or is a pharmaceutically acceptable salt, solvate, clathrate or prodrug thereof, wherein X is $OR_3$. In certain embodiments, $R_3$ is optionally substituted $C_1$-$C_{10}$ alkyl, optionally substituted $C_3$-$C_{12}$ cycloalkyl, optionally substituted $C_3$-$C_{12}$ cycloalkenyl, optionally substituted heterocyclic, optionally substituted aryl or optionally substituted heteroaryl. In other aspects, $R_3$ is optionally substituted $C_1$-$C_{10}$ alkyl.

In another embodiment, the invention is directed a compound of Formula (Ib), or is a pharmaceutically acceptable salt, solvate, clathrate or prodrug thereof, wherein X is $S(O)_2NR_aR_b$. In some embodiments, $R_a$ and $R_b$ are each independently hydrogen or optionally substituted $C_1$-$C_{10}$ alkyl.

In yet another embodiment, the invention is directed a compound of Formula (Ib), or is a pharmaceutically acceptable salt, solvate, clathrate or prodrug thereof, wherein X is $C(O)NR_aS(O)_2R_3$.

In yet another embodiment, the compound has the Formula (Ib), or is a pharmaceutically acceptable salt, solvate, clathrate or prodrug thereof, wherein m is 0 or 1.

In a further aspect, the compound has the Formula (Ib), or is a pharmaceutically acceptable salt, solvate, clathrate or prodrug thereof, wherein n is 0, 1 or 2. In certain embodiments, n is 1.

It is to be understood that the specific embodiments described herein can be taken in combination with other specific embodiments delineated herein. For example, for compounds of Formula (I), A was defined as sulfur in certain embodiments and in certain embodiments, each of $R_{4a}$ and $R_{4b}$ was defined as independently selected from hydrogen and optionally substituted $C_1$-$C_{10}$ alkyl. It is thus to be understood that the invention encompasses compounds of Formula (I), wherein A is sulfur and each of $R_{4a}$ and $R_{4b}$ are each independently selected from hydrogen and optionally substituted $C_1$-$C_{10}$ alkyl.

Exemplary compounds encompassed by the invention are shown below and in Tables 1, 2 and 3 below:

TABLE 1

| Compound No. | Compound |
| --- | --- |
| 1 | 2-(4-(Cyclopropyl(methyl)amino)-5,6,7,8-tetrahydrobenzo[4,5]thieno[2,3-d]pyrimidin-2-yl)-N-methylacetamide |

TABLE 1-continued

| Compound No. | Compound |
|---|---|
| 2 | 2-(4-(Cyclopropyl(methyl)amino)-5,6,7,8-tetrahydrobenzo[4,5]thieno[2,3-d]pyrimidin-2-yl)acetic acid |
| 3 | 2-(4-(Cyclopropyl(methyl)amino)-5,6,7,8-tetrahydrobenzo[4,5]thieno[2,3-d]pyrimidin-2-yl)-N,N-dimethylacetamide |
| 4 | Cyclopropyl-(2-methoxymethyl-5,6,7,8-tetrahydro-benzo[4,5]thieno[2,3-d]pyrimidin-4-yl)-methyl-amine |

TABLE 2

| Compound No. | Compound |
|---|---|
| 5 | 2-(4-(Cyclopropyl(methyl)amino)-5,6,7,8-tetrahydrobenzo[4,5]thieno[2,3-d]pyrimidin-2-yl)acetamide |

TABLE 2-continued

| Compound No. | Compound |
|---|---|
| 6 | 2-[4-(Cyclopropyl-methyl-amino)-5,6,7,8-tetrahydro-benzo[4,5]thieno[2,3-d]pyrimidin-2-yl]-1-pyrrolidin-1-yl-ethanone |
| 7 | 2-[4-(Cyclopropyl-methyl-amino)-5,6,7,8-tetrahydro-benzo[4,5]thieno[2,3-d]pyrimidin-2-yl]-1-(3,3-difluoro-pyrrolidin-1-yl)-ethanone |
| 8 | 2-[4-(Cyclopropyl-methyl-amino)-5,6,7,8-tetrahydro-benzo[4,5]thieno[2,3-d]pyrimidin-2-yl]-1-(3-dimethylamino-pyrrolidin-1-yl)-ethanone |
| 9 | 2-[4-(Cyclopropyl-methyl-amino)-5,6,7,8-tetrahydro-benzo[4,5]thieno[2,3-d]pyrimidin-2-yl]-1-morpholin-4-yl-ethanone |

TABLE 2-continued

| Compound No. | Compound |
|---|---|
| 10 | 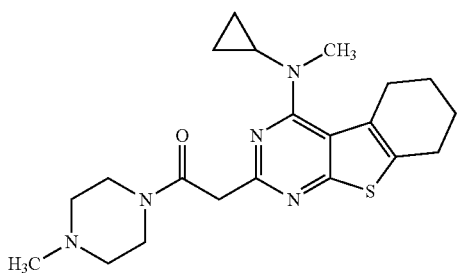 [SMILES: CN1CCN(C(=O)Cc2nc(N(C)C3CC3)c3c4c(sc3n2)CCCC4)CC1]
2-[4-(Cyclopropyl-methyl-amino)-5,6,7,8-tetrahydro-benzo[4,5]thieno[2,3-d]pyrimidin-2-yl]-1-(4-methyl-piperazin-1-yl)-ethanone |
| 11 | 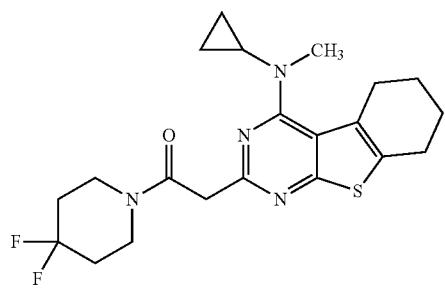 [SMILES: CN(c1nc(CC(=O)N2CCC(F)(F)CC2)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-(4,4-difluoro-piperidin-1-yl)-ethanone |
| 12 | 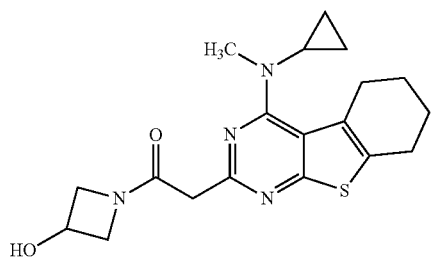 [SMILES: CN(c1nc(CC(=O)N2CC(O)C2)nc2sc3c(c12)CCCC3)C1CC1]
2-(4-(Cyclopropyl(methyl)amino)-5,6,7,8-tetrahydrobenzo[4,5]thieno[2,3-d]pyrimidin-2-yl)-1-(3-hydroxyazetidin-1-yl)ethanone |
| 13 | 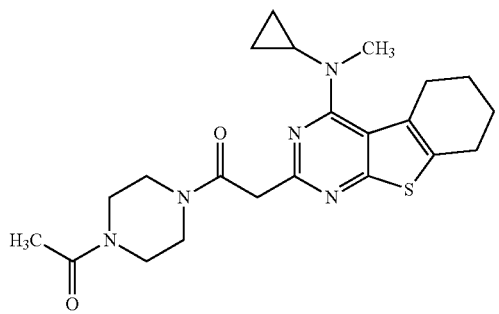 [SMILES: CC(=O)N1CCN(C(=O)Cc2nc(N(C)C3CC3)c3c4c(sc3n2)CCCC4)CC1]
1-(4-Acetyl-piperazin-1-yl)-2-[4-(Cyclopropyl-methyl-amino)-5,6,7,8-tetrahydro-[1]benzothieno[2,3-d]pyrimidin-2-yl]-ethanone |
| 14 | 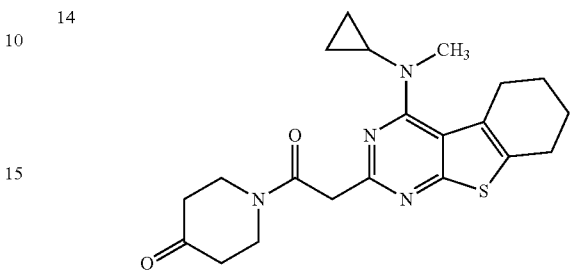
1-{2-[4-(Cyclopropyl-methyl-amino)-5,6,7,8-tetrahydro-benzo[4,5]thieno[2,3-d]pyrimidin-2-yl]-acetyl}-piperidin-4-one |
| 15 | 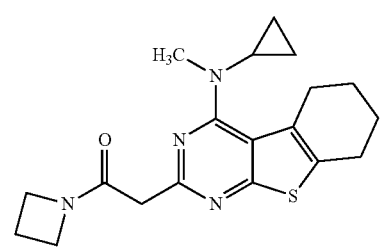 [SMILES: CN(c1nc(CC(=O)N2CCC2)nc2sc3c(c12)CCCC3)C1CC1]
1-(Azetidin-1-yl)-2-(4-(cyclopropyl(methyl)amino)-5,6,7,8-tetrahydrobenzo[4,5]thieno[2,3-d]pyrimidin-2-yl)ethanone |
| 16 | 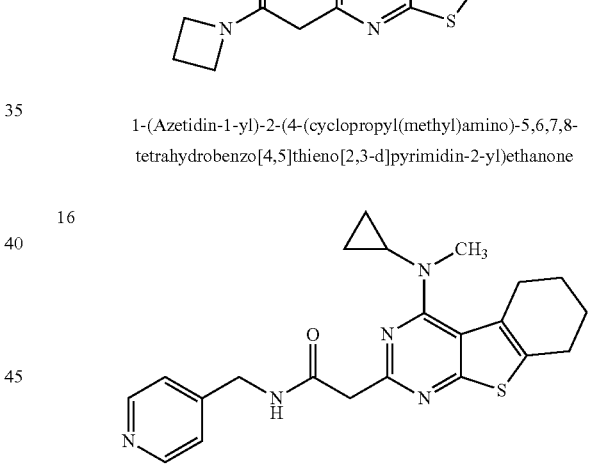
2-[4-(Cyclopropyl-methyl amino)-5,6,7,8-Tetrahydrobenzo(4,5)thieno(2,3-d)pyrimidin]-N-yridin-4-ylmethyl)-acetamide |
| 17 | 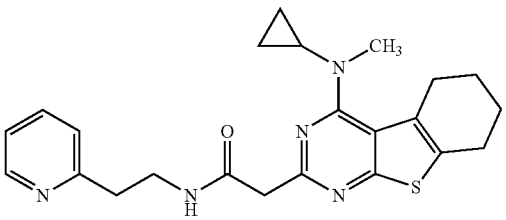 [SMILES: CN(c1nc(CC(=O)NCCc2ccccn2)nc2sc3c(c12)CCCC3)C1CC1]
2-[4-(Cyclopropyl-methylamino)-5,6,7,8-tetrahydrobenzo(4,5)thieno(2,3-d)pyrimidin]-pyrimidin-2-yl)-N-(2-pyridin-2-yl-ethyl)-acetamide |

TABLE 2-continued

| Compound No. | Compound |
|---|---|
| 18 | 2-[4-(Cyclopropyl-methyl amino)-5,6,7,8-tetrahydrobenzo(4,5)thieno(2,3-d)pyrimidin]-pyrimidin-2-yl]-N-pyridin-2-yl-methylacetamide |
| 19 | 2-(4-(Cyclopropyl-methyl amino)-5,6,7,8-tetrahydrobenzo(4,5)thieno(2,3-d)pyrimidin)-N-yridin-2-ylmethyl)-acetamide |
| 20 | (S)-2-(4-(Cyclopropyl(methyl)amino)-5,6,7,8-tetrahydrobenzo[4,5]thieno[2,3-d]pyrimidin-2-yl)-1-(3-(2-hydroxypropan-2-yl)pyrrolidin-1-yl)ethanone |
| 21 | 2-[4-(Cyclopropyl-methyl amino)-5,6,7,8-tetrahydrobenzo(4,5)thieno(2,3-d)pyrimidin]-2-yl]-N-(2-pyridin-4-yl-ethyl)-acetamide |
| 22 | 2-[4-(Cyclopropyl-methyl amino)-5,6,7,8-tetrahydrobenzo(4,5)thieno(2,3-d)pyrimidin]-2-yl]-N-(2-pyridin-4-yl-ethyl)-acetamide |
| 23 | 2-[4-(Cyclopropyl-methyl amino)-5,6,7,8-tetrahydrobenzo(4,5)thieno(2,3-d)pyrimidin]-pyridin-2-yl]-N-(2-pyridin-3-yl-ethyl)-acetamide |
| 24 | 2-[4-(Cyclopropyl-methyl-amino)-5,6,7,8-tetrahydrobenzo[4,5]thieno[2,3-d]pyrimidin-2yl]-1-((S)-3-dimethylamino-pyrrolidin-1-yl)-ethanone |
| 25 | 2-[4-(Cyclopropyl-methyl-amino)-5,6,7,8-tetrahydro-benzo[4,5]thieno[2,3-d]pyrimidin-2yl]-1-(3-methanesulfonyl-pyrrolidin-1-yl)-ethanone |

TABLE 2-continued

| Compound No. | Compound |
|---|---|
| 26 | 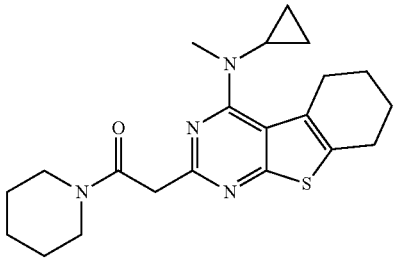 [SMILES: CN(c1nc(CC(=O)N2CCCCC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2yl]-1-piperidin-1-yl-ethanone |
| 27 | 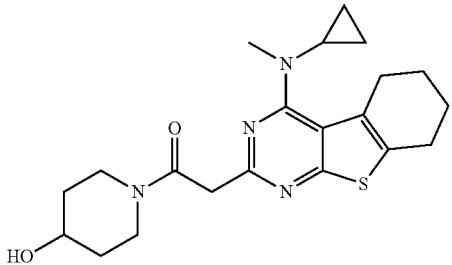 [SMILES: CN(c1nc(CC(=O)N2CCC(O)CC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-(4-hydroxy-piperidin-1-yl)-ethanone |
| 28 | 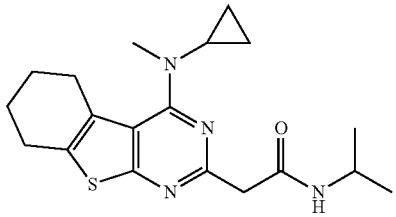 [SMILES: CC(C)NC(=O)Cc1nc(N(C)C2CC2)c2c3c(sc2n1)CCCC3]<br>2-[4-(Cyclopropyl-methyl-amino)-5,6,7,8-tetrahydro-benzo[4,5]thieno[2,3-d]pyrimidin-2-yl]-N-isopropyl-acetamide |
| 29 | 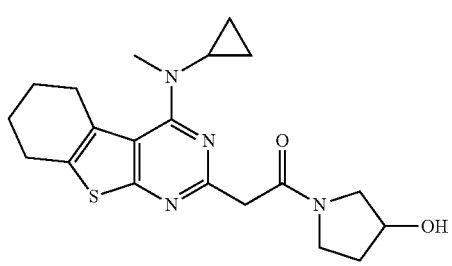 [SMILES: CN(c1nc(CC(=O)N2CCC(O)C2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-(3-hydroxy-pyrrolidin-1-yl)-ethanone |
| 30 | 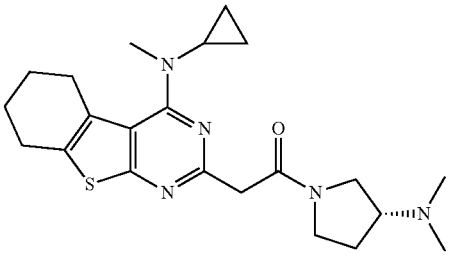 [SMILES: CN(c1nc(CC(=O)N2CC[C@@H](N(C)C)C2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-((R)-3-dimethylamino-pyrrolidin-1-yl)-ethanone |
| 31 | 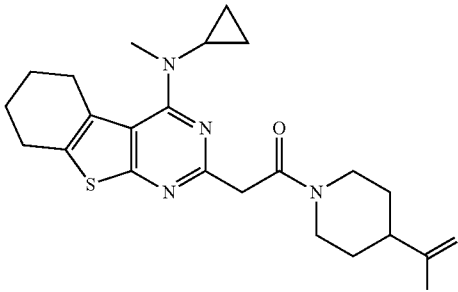<br>1-{2-[4-(Cyclopropyl-methyl-amino)-5,6,7,8-tetrahydro-benzo[4,5]thieno[2,3-d]pyrimidin-2-yl]-acetyl}-piperidine-4-carboxylic acid amide |
| 32 | 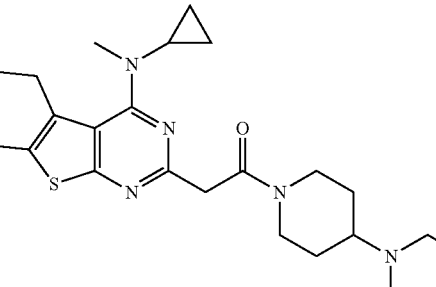<br>2-[4-(Cyclopropyl-methyl-amino)-5,6,7,8-tetrahydro-benzo[4,5]thieno[2,3-d]pyrimidin-2-yl]-1-(4-morpholin-4-yl-piperidin-1-yl)-ethanone |
| 33 | 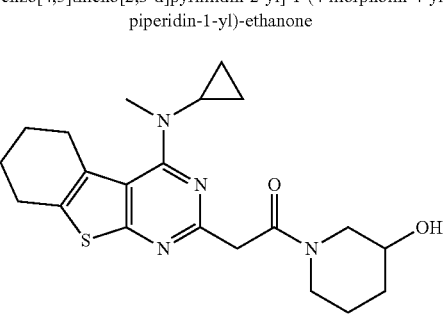<br>2-[4-(Cyclopropyl-methyl-amino)-5,6,7,8-tetrahydro-benzo[4,5]thieno[2,3-d]pyrimidin-2-yl]-1-(3-hydroxy-piperidin-1-yl)-ethanone |

TABLE 2-continued

| Compound No. | Compound |
|---|---|
| 34 | 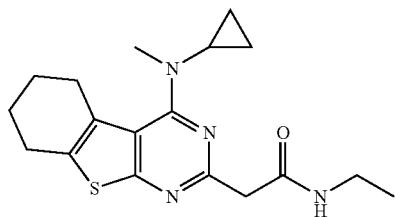 [SMILES: CCNC(=O)Cc1nc(N(C)C2CC2)c2c3c(sc2n1)CCCC3]
2-[4-(Cyclopropyl-methyl-amino)-5,67,8-tetrahydro-benzo[4,5]thieno[2,3-d]pyrimidin-2-yl]-N-ethyl-acetamide |
| 35 | 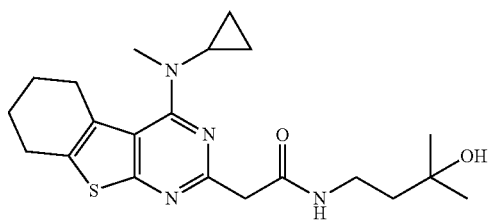 [SMILES: CN(c1nc(CC(=O)NCCC(C)(C)O)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-N-(3-hydroxy-3-methyl-butyl)-acetamide |
| 36 | 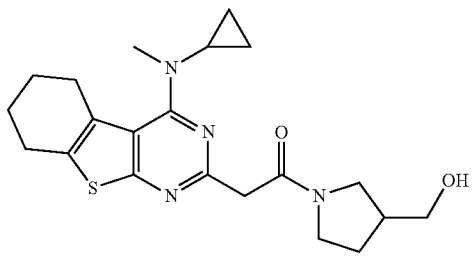 [SMILES: CN(c1nc(CC(=O)N2CCC(CO)C2)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-(3-hydroxymethyl-pyrrolidin-1-yl)-ethanone |
| 37 | 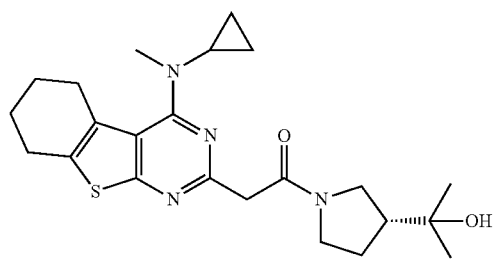 [SMILES: CN(c1nc(CC(=O)N2CC[C@@H](C(C)(C)O)C2)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-[(R)-3-(1-hydroxy-1-methyl-ethyl)-pyrrolidin-1-yl]-ethanone |

TABLE 2-continued

| Compound No. | Compound |
|---|---|
| 38 | 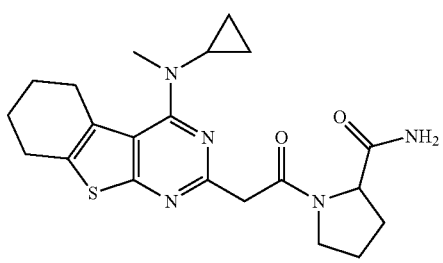 [SMILES: CN(c1nc(CC(=O)N2CCCC2C(N)=O)nc2sc3c(c12)CCCC3)C1CC1]
1-(2-(4-(Cyclopropyl(methyl)amino)-5,6,7,8-tetrahydrobenzo[4,5]thieno[2,3-d]pyrimidin-2-yl)acetyl)pyrrolidine-2-carboxamide |
| 39 | 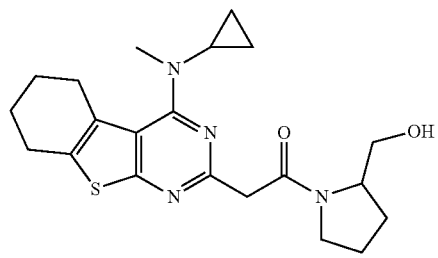 [SMILES: CN(c1nc(CC(=O)N2CCCC2CO)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-(2-hydroxymethyl-pyrrolidin-1-yl)-ethanone |
| 47 | 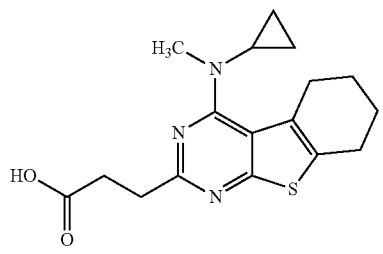 [SMILES: CN(c1nc(CCC(=O)O)nc2sc3c(c12)CCCC3)C1CC1]
3-[4-(Cyclopropyl-methyl-amino)-5,6,7,8-tetrahydro-[1]benzothiopheno[2,3-d]pyrimidin-2-yl]-propionic acid |
| 48 | 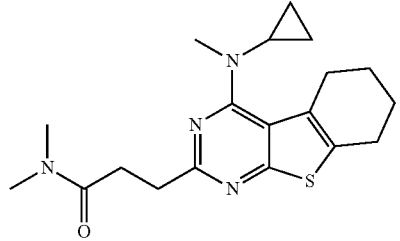 [SMILES: CN(C)C(=O)CCc1nc(N(C)C2CC2)c2c3c(sc2n1)CCCC3]
3-[4-(Cyclopropyl-methyl-amino)-5,6,7,8-tetrahydro-[1]benzothiopheno[2,3-d]pyrimidin-2-yl]-N,N-dimethyl-propionamide |

TABLE 2-continued

| Compound No. | Compound |
|---|---|
| 49 | 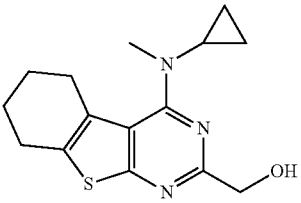 [SMILES: CN(c1nc(CO)nc2sc3c(c12)CCCC3)C1CC1]<br>[4-(Cyclopropyl-methyl-amino)-5,6,7,8-tetrahydro-benzo[4,5]thieno[2,3-d]pyrimidin-2-yl]-methanol |
| 50 | 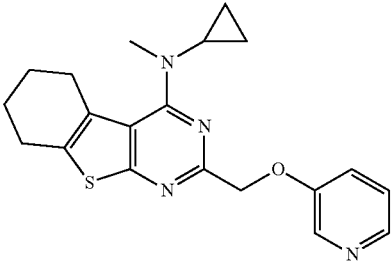 [SMILES: CN(c1nc(COc2cccnc2)nc2sc3c(c12)CCCC3)C1CC1]<br>Cyclopropyl-methyl-[2-(pyridine-3-yloxymethyl)-5,6,7,8-tetrahydro-benzo[4,5]thieno[2,3-d]pyrimidin-4-yl]-amine |
| 51 | 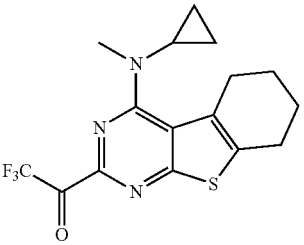 [SMILES: CN(c1nc(C(=O)C(F)(F)F)nc2sc3c(c12)CCCC3)C1CC1]<br>3-[4-(Cyclopropyl-methyl-amino)-5,6,7,8-tetrahydrobenzo[4,5]thieno[2,3-d]pyrimidin-2-yl]-1,1,1-trifluoro-propan-2-one |
| 52 | 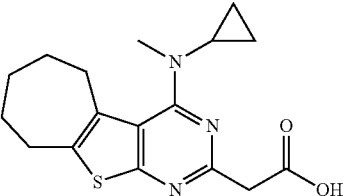 [SMILES: CN(c1nc(CC(=O)O)nc2sc3c(c12)CCCCC3)C1CC1]<br>[4-(Cyclopropyl-methyl-amino)-6,7,8,9-tetrahydro-5H-10-thia-1,3-diazabenz[a]azulen-2-yl]-acetic acid |
| 53 | 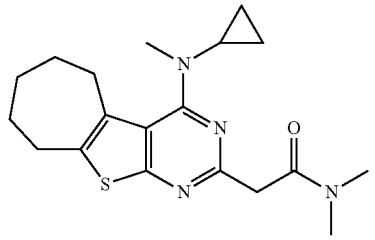 [SMILES: CN(C)C(=O)Cc1nc(N(C)C2CC2)c2c3c(sc2n1)CCCCC3]<br>2-[4-(Cyclopropyl-methyl-amino)-6,7,8,9-tetrahydro-5H-10-thia-1,3-diaza-benz[a]azulen-2-yl]-N,N-dimethyl-acetamide |

TABLE 3

| Compound No. | Compound |
|---|---|
| 40 | 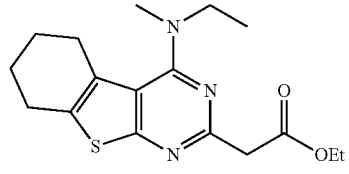 [SMILES: CCOC(=O)Cc1nc(N(C)CC)c2c3c(sc2n1)CCCC3]<br>[4-(Ethyl-methyl-amino)-5,6,7,8-tetrahydro-benzo[4,5]thieno[2,3-d]pyrimidin-2-yl]-acetic acid ethyl ester |
| 41 | 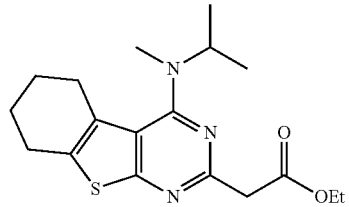 [SMILES: CCOC(=O)Cc1nc(N(C)C(C)C)c2c3c(sc2n1)CCCC3]<br>[4-(Isopropyl-methyl-amino)-5,6,7,8-tetrahydro-benzo[4,5]thieno[2,3-d]pyrimidin-2-yl]-acetic acid ethyl ester |
| 42 | 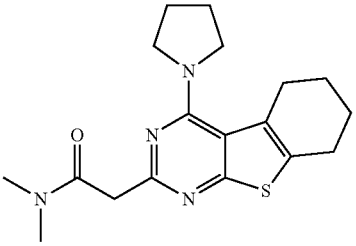 [SMILES: CN(C)C(=O)Cc1nc(N2CCCC2)c2c3c(sc2n1)CCCC3]<br>N,N-Dimethyl-2-(4-pyrrolidin-1-yl-5,6,7,8-tetrahydro-benzo[4,5]thieno[2,3-d]pyrimidin-2-yl)-acetamide |
| 43 | 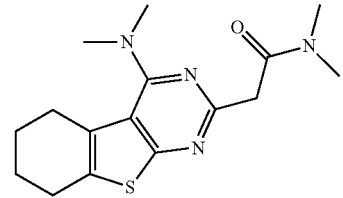 [SMILES: CN(C)C(=O)Cc1nc(N(C)C)c2c3c(sc2n1)CCCC3]<br>2-(4-Dimethylamino-5,6,7,8-tetrahydro-benzo[4,5]thieno[2,3-d]pyrimidin-2-yl)-N,N-dimethyl-acetamide |
| 44 | 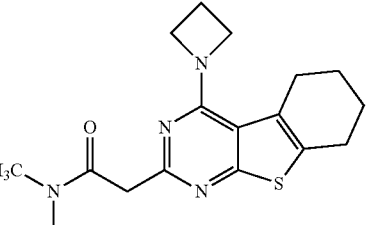<br>2-(4-(Azetidin-1-yl)-5,6,7,8-tetrahydrobenzo[4,5]thieno[2,3-d]pyrimidin-2-yl)-N,N-dimethylacetamide |

TABLE 3-continued

| Compound No. | Compound |
|---|---|
| 45 | 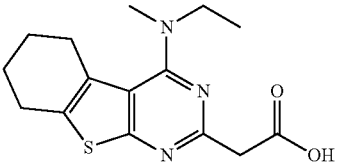 [SMILES: CCN(C)c1nc(CC(=O)O)nc2sc3c(c12)CCCC3] [4-(Ethyl-methyl-amino)-5,6,7,8-tetrahydro-benzo[4,5]thieno[2,3-d]pyrimidin-2-yl]-acetic acid |
| 46 | 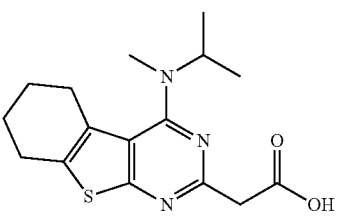 [SMILES: CC(C)N(C)c1nc(CC(=O)O)nc2sc3c(c12)CCCC3] [4-(Isopropyl-methyl-amino)-5,6,7,8-tetrahydro-benzo[4,5]thieno[2,3-d]pyrimidin-2-yl]-acetic acid. |

As used herein, the term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to monocyclic and polycyclic alkyl moieties having 3 or more carbon atoms. Polycyclic alkyl moieties include, for example, bicycloalkyl and tricyclcoalkyl. Examples of cycloalkyl include, but are not limited to, cyclopropyl, cyclobutyl, cyclopentyl, cyclohexyl, cycloheptyl and adamantyl.

The term "cycloalkenyl," as used herein, refers to monocyclic and polycyclic alkenyl moieties having 3 or more carbon atoms.

The term "cycloalkynyl," as used herein, refers to monocyclic and polycyclic alkynyl moieties having 5 or more carbon atoms.

The term "heterocyclic" encompasses heterocycloalkyl, heterocycloalkenyl, heterobicycloalkyl, heterobicycloalkenyl, heteropolycycloalkyl, heteropolycycloalkenyl and the like. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkyl groups containing one or more heteroatoms (O, S or N) within a ring.

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. A polycyclic heteroaryl can comprise fused rings, covalently attached rings or a combination thereof. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached).

The term "alkoxy" refers to a radical wherein an alkyl moiety is attached via an oxygen atom. Non-limiting examples of such groups include methoxy, ethoxy, propoxy, butoxy, pentoxy, hexoxy and the like.

The term "substituted" refers to substitution by independent replacement of one, two, or three or more of the hydrogen atoms with substituents including, but not limited to, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —C(O)$R_y$, —C(O)C(O)$R_y$, —$OCO_2R_y$, —OC(O)$R_y$, OC(O)C(O) $R_y$, —NHC(O)$R_y$, —$NHCO_2R_y$, —NHC(O)C(O)$R_y$, NHC (S)$NH_2$, —NHC(S)$NHR_x$, —NHC(NH)$NH_2$, —NHC(NH) $NHR_x$, —NHC(NH)$R_x$, —C(NH)$NHR_x$, —$NR_xC(O)R_y$, —$NR_xCO_2R_y$, —$NR_xC(O)C(O)R_y$, —$NR_xC(S)NH_2$, —$NR_xC(O)NR_xR_x$, —$NR_xS(O)_2NR_xR_x$, —$NR_xC(S)NHR_x$, —$NR_xC(NH)NH_2$, —$NR_xC(NH)NHR_x$, —$NR_xC(NH)R_x$, —C($NR_x$)$NHR_x$—S(O)$_n$$R_y$, —$NHSO_2R_x$, —$CH_2NH_2$, —$CH_2SO_2CH_3$, (C=$NR_x$)$R_x$; -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic; —$R_y$ is selected from the group consisting of —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic, and n is 0, 1 or 2. It is understood that the aryls, heteroaryls, alkyls, and the like can be further substituted.

The term "haloalkyl" as used herein refers to an alkyl group having 1 to (2m+1) subsistent(s) independently selected from F, Cl, Br or I, where n is the maximum number of carbon atoms in the alkyl group.

Non-limiting examples of optionally substituted aryl are phenyl, substituted phenyl, napthyl and substituted naphthyl.

Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R--S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

Likewise, all tautomeric forms are also intended to be included. Where a particular compound is described or depicted it is intended to encompass that chemical structure as well as tautomers of that structure.

It is to be understood that atoms making up the compounds of the present invention are intended to include isotopic forms of such atoms. Isotopes, as used herein, include those atoms having the same atomic number but different mass numbers. Isotopes of hydrogen include, for example, tritium and deuterium, and isotopes of carbon include, for example, $^{13}C$ and $^{14}C$. The invention therefore encompasses embodiments in which one or more of the hydrogen atoms in Formula (I), (Ia), or (Ib) are replaced with deuterium. The invention also encompasses embodiments wherein one or more of the carbon atoms in Formula (I), (Ia), or (Ib) is replaced with silicon atoms.

The invention additionally encompasses embodiments wherein one or more of the nitrogen atoms in Formula (I), (Ia), or (Ib) are oxidized to N-oxide.

An exemplary synthetic route for the preparation of compounds of the invention is shown in the Schemes I and II below. As will be understood by the skilled artisan, diastereomers can be separated from the reaction mixture using column chromatography.

Scheme I:

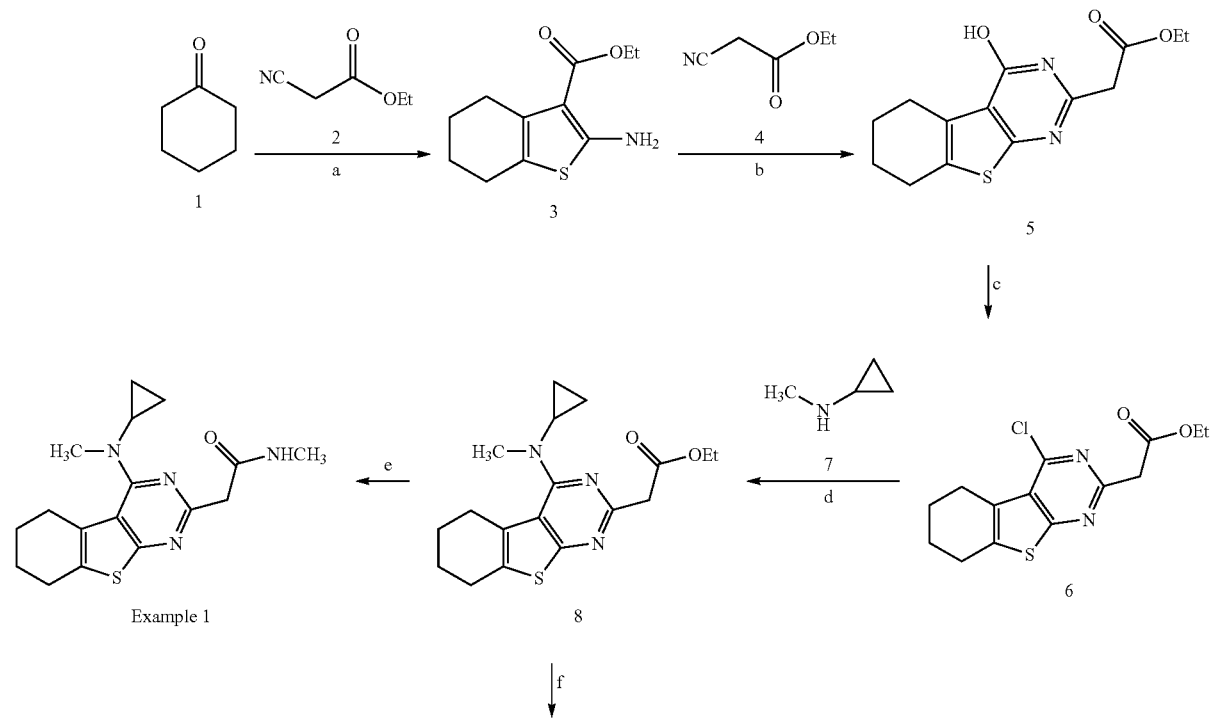

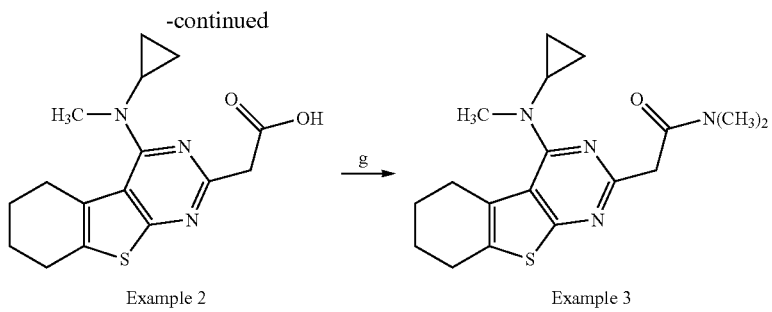

Example 2 → Example 3 a) 1, 2, sulfur, DEA, EtOH, 0° C. to 45° C.;
b) 4, HCl(g), RT;
c) POCl₃, reflux;
d) 7, TEA, EtOH, RT;
e) 40% CH₃NH₂ (aq.), EtOH, RT;
f) LiOH-H₂O, THF:H₂O (9:1), RT;
g) 2M (CH₃)₂NH/THF, HOBt, EDC-HCl, 0° C. to RT.

Scheme II:

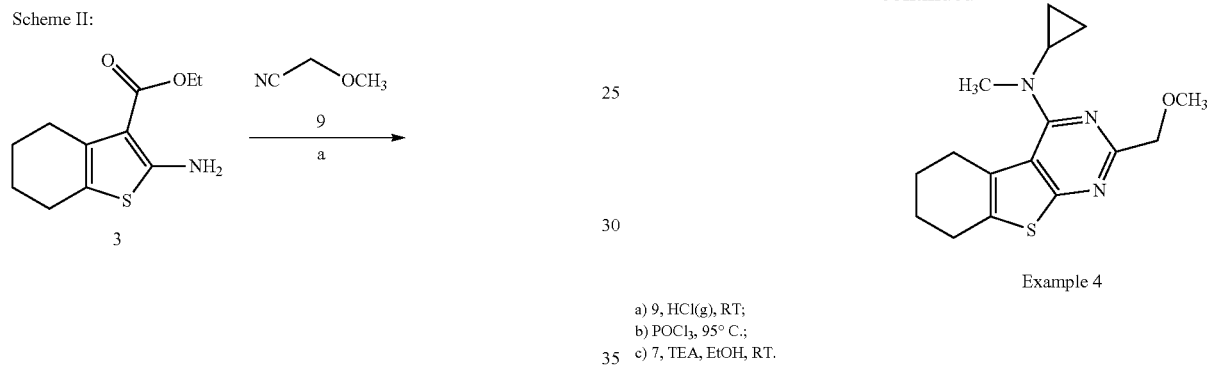

Example 4 a) 9, HCl(g), RT;
b) POCl₃, 95° C.;
c) 7, TEA, EtOH, RT.

The invention encompasses pharmaceutically acceptable salts of the compounds described herein. Thus, in certain aspects, the invention is directed to pharmaceutically acceptable salts of compounds of the invention and pharmaceutical compositions thereof. A "pharmaceutically acceptable salt" includes an ionic bond-containing product of the reaction between the disclosed compound with either an acid or a base, suitable for administering to a subject. Pharmaceutically acceptable salts are well known in the art and are described, for example, in Berge et al. (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —C(O)OH or —SO₃H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The invention also includes hydrates of the compounds described herein, including, for example, solvates of the compounds described herein, pharmaceutical compositions comprising the solvates and methods of use of the solvates. In some embodiments, the invention is a solvate of a compound of Formula (I), (Ia), or (Ib) or a pharmaceutical composition thereof.

Also included in the present invention are prodrugs of the compounds described herein, for example, prodrugs of a compound of Formula (I), (Ia), or (Ib) or a pharmaceutical composition thereof or method of use of the prodrug.

The invention additionally includes clathrates of the compounds described herein, pharmaceutical compositions comprising the clathrates, and methods of use of the clathrates. In some embodiments, the invention is directed to clathrates of a compound of Formula (I), (Ia), or (Ib) or a pharmaceutical composition thereof.

The invention encompasses a method of inhibiting deubiquitination activity of a Usp14 protein comprising contacting the Usp14 protein with a compound described herein, or a pharmaceutically acceptable salt, solvate, clathrate or prodrug thereof, in an amount sufficient to inhibit deubiquitination activity of the Usp14 protein.

The invention also encompasses a method of enhancing protein degradation by a proteasome in a cell comprising contacting the cell with a compound of a compound described herein, or a pharmaceutically acceptable salt, solvate, clathrate or prodrug thereof, in an amount sufficient to enhance protein degradation by the proteasome.

As discussed above, the invention includes pharmaceutical compositions comprising a pharmaceutically acceptable carrier or excipient and a compound described herein. The compounds of Formula (I), (Ia), or (Ib), or a pharmaceutically acceptable salt, solvate, clathrate or prodrug, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising compounds of Formula (I), (Ia), or (Ib), or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes.

[Paul et al., Eur. J. Immunol. 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention also encompasses a method of treating a patient suffering from a condition associated with a dysfunction in protein homeostasis comprising administering to said patient a therapeutically effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a therapeutic agent, an "effective amount" of the therapeutic agent that is sufficient to ameliorate of one or more symptoms of a disorder and/or prevent advancement of a disorder, cause regression of the disorder and/or to achieve a desired effect.

As used herein, the term "inhibiting" or "decreasing" encompasses causing a net decrease by either direct or indirect means. The term "increasing" or "enhancing" means to cause a net gain by either direct or indirect means.

The invention encompasses the treatment of a condition associated with a dysfunction in proteostasis. Proteostasis refers to protein homeostasis. Dysfunction in protein homeostasis is a result of protein misfolding, protein aggregation, defective protein trafficking or protein degradation. Exemplary proteins of which there can be a dysfunction in proteostasis, for example that can exist in a misfolded state, include, but are not limited to, glucocerebrosidase, hexosamine A, cystic fibrosis transmembrane conductance regulator, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, Aβ peptide, tau protein, transthyretin, insulin, TAR DNA-binding protein 43 (TDP-43), ataxin-3, and rhodopsin.

In certain embodiments, the protein is selected from the group consisting of huntingtin, tau, alpha-synuclein, α1 antitrypsin and superoxide dismutase.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IB-MPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, the disease associated with a dysfunction in proteostasis is a cardiovascular disease. Cardiovascular diseases include, but are not limited to coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In some embodiments, the condition associated with a dysfunction in proteostasis is selected from the group consisting of Huntington's disease, Alzheimer's disease, Parkinson's disease, amyotrophic lateral sclerosis, diabetes and complications thereof, ocular diseases and cancer or tumor.

Additional conditions associated with a dysfunction of proteostasis include hemoglobinopathies, inflammatory diseases, intermediate filament diseases, drug-induced lung damage and hearing loss. The invention also encompasses methods for the treatment of hemoglobinopathies (such as sickle cell anemia), an inflammatory disease (such as inflammatory bowel disease, colitis, ankylosing spondylitis), intermediate filament diseases (such as non alcoholic and alcoholic fatty liver disease) and drug induced lung damage (such as methotrexate-induced lung damage).

The invention additionally encompasses methods for treating hearing loss, such as noise-induced hearing loss, aminoglycoside-induced hearing loss, and cisplatin-induced hearing loss.

In addition to conditions associated with a dysfunction in proteostasis, the compound of the present invention can be used to treat a disease or condition characterized by deficient proteasome activity or deficient activity of other components of the ubiquitin-proteasome pathway. Such conditions include, for example, Hippel-Lindau disease, spino-cerebellar ataxia 1, Angelman syndrome, giant axon neuropathy, inclusion body myopathy with Paget disease, and frontotemporal dementia.

In certain embodiments, the invention encompasses a method for the treatment of a condition selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, prion diseases and autism.

In certain embodiments, the invention includes methods for the treatment of a condition associated with a dysfunction in proteostasis comprising administering to a patient in need thereof an effective amount of a compound of Formula (I), (Ia) or (Ib), or a pharmaceutically acceptable salt, solvate, clathrate or prodrug, or the compounds described herein, and a second agent (e.g., a second therapeutic agent). Co-administered agents, compounds, or therapeutics need not be administered at exactly the same time. In certain embodiments, however, the compound encompassed Formula (I), (Ia), or (Ib), or a pharmaceutically acceptable salt, solvate, clathrate or prodrug, or a compound described herein, is administered substantially simultaneously as the second agent. By "substantially simultaneously," it is meant that the compound of Formula (I), (Ia), or (Ib), or a pharmaceutically acceptable salt, solvate, clathrate or prodrug, or a compound described herein, is administered before, at the same time, and/or after the administration of the second agent, and encompasses, for example, administration within the same treatment session or as part of the same treatment regimen. Exemplary second agents include pharmacologic chaperones and proteostasis regulators (such as, those described below).

In yet additional aspects, the invention encompasses a method for treating a condition characterized by deficient proteasome activity or deficiency of other components of the ubiquitin-proteasome pathway in a subject comprising administering to said subject an effective amount of a compound of the invention, or a pharmaceutically acceptable salt, solvate, clathrate or prodrug thereof.

In an additional embodiment, the invention is directed to a pharmaceutical composition comprising a compound of Formula (I), (Ia), or (Ib), or a pharmaceutically acceptable salt, solvate, clathrate or prodrug, and a second agent, wherein the second agent is selected from the group consisting of a pharmacologic chaperone and a proteostasis regulator. The invention also encompasses a method of treating a patient suffering from a condition associated with a dysfunction in proteostasis comprising administering a therapeutically effective amount of a compound of the invention and a second agent, wherein the second agent is a pharmacologic chaperone. Pharmacologic chaperones or kinetic stabilizers refer to compounds that bind an existing steady state level of the folded mutant protein and chemically enhance the folding equilibrium by stabilizing the fold [Bouvier, Chem Biol 14: 241-242, 2007; Fan et al., Nat Med 5: 112-115, 1999; Sawkar et al., Proc Natl Acad Sci USA 99:15428-15433, 2002; Johnson and Kelly, Accounts of Chemical Research 38: 911-921, 2005]. The pharmacologic chaperone is administered in amount that in combination with a compound described herein in an amount that is sufficient to treat a patient suffering from a condition associated with a dysfunction in proteostasis. Exemplary pharmacologic chaperones are described in U.S. Patent Application Publication No's. 20080056994, 20080009516, 20070281975, 20050130972, 20050137223, 20050203019, 20060264467 and 20060287358, the contents of each of which are incorporated by reference herein.

In another embodiment, the invention is a method of treating a patient suffering from a condition associated with a dysfunction in proteostasis comprising administering to said patient an effective amount of a compound described herein and a second agent, wherein the second agent is a proteostasis regulator. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the heat shock response (HSR) signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., J Biol Chem, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol. In certain aspects, the proteostasis regulator is a heat shock response activator. A heat shock response activator is an agent that indirectly or directly activates the heat shock response, for example, by directly or indirectly activating heat shock transcription factor 1 (HSF1), inhibiting Hsp90, and/or activating chaperone expression [Westerheide et al., J Biol Chem, 2004. 279(53): p. 56053-60], the contents of which are expressly incorporated by reference herein. The terms "heat shock response activator," "heat shock activator," "heat shock response inducer," and "heat shock inducer" are used interchangeably herein. Non-limiting examples of heat shock response activators are celastrols, non-steroidal anti-inflammatory drugs, ansamycin, geldenamycin, radiciol, glucuronic acid, and tributylin. Heat shock response activators have also been described, for example, in U.S. Patent Application Publication No's. 20070259820, 20070207992, 20070179087, 20060148767, the contents of each of which are expressly incorporated by reference herein. In some embodiments, the heat shock response activator is a small molecule heat shock response activator.

The invention also encompasses a method of treating cancer or a tumor in a patient in need thereof comprising administering to said patient an effective amount of a compound of Formula (I), (Ia), or (Ib). The invention additionally encompasses a method of treating cancer or a tumor in a patient in need thereof comprising administering to said patient an effective amount of a compound described herein. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering a compound of Formula (I), (Ia), or (Ib) or a compound described herein in combination with the administration of a chemotherapeutic agent. Chemotherapeutic agents that can be utilized include, but are not limited to, alkylating agents such as cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising administering to a patient in need thereof an effective amount of a compound of Formula (I), (Ia), or (Ib) or a compound described herein in combination with radiation therapy.

In yet an additional embodiment, the invention is a method of treating a viral infection comprising administering to a subject in need thereof an effective amount of a compound of Formula (I), (Ia), or (Ib), or a compound described herein. In certain embodiments, the viral infection is an infection from a virus of the flavivirus family. Examples of viruses in the flavivirus family include, for example, Dengue virus, West Nile virus, Japanese encephalitis virus, yellow fever virus and tick-borne encephalitis viruses. In an additional embodiment, the virus is the La Crosse virus. In another embodiment, the virus is Dengue virus or West Nile virus.

The invention is illustrated by the following examples which are not meant to be limiting in any way.

EXEMPLIFICATION

Example 1

2-(4-(Cyclopropyl(methyl)amino)-5,6,7,8-tetrahydrobenzo[4,5]thieno[2,3-d]pyrimidin-2-yl)-N-methylacetamide (Compound 1)

To a stirred solution of ethyl cyanoacetate (10.82 ml, 0.1018 mol) in 100 ml absolute ethanol was added sulfur powder (3.42 gm, 0.1018 mol)—followed by cyclohexanone (10 gm, 0.1018 mol) at room temperature under $N_2$ atmosphere; the resulting mixture was cooled to 0-5° C. DEA (11.3 ml, 0.1018 mol) was added to this mixture and then reaction was warmed to room temperature and then stirred at 40-45° C. for 2-3 h. The reaction was judged complete by TLC. Reaction mass was kept for 30 minutes at 0° C., solid precipitated out was filtered through Buchner funnel and washed with chilled ethanol (2×50 ml) which was then dried in a rotary evaporator to give ethyl 2-amino-4,5,6,7-tetrahydrobenzo[b]thiophene-3-carboxylate as a white solid which was used as such for the next reaction without further purification. Yield: (15 g, 78.53%); $^1$H NMR (400 MHz, CDCl$_3$) δ ppm=5.91 (br, 2H), 4.27-4.21 (q, 2H), 2.70-2.67 (m, 2H), 2.50-2.47 (m, 2H), 1.79-1.69 (m, 4H), 1.33-130 (t, 3H); LCMS [M+H]=226.2.

The ethyl 2-amino-4,5,6,7-tetrahydrobenzo[b]thiophene-3-carboxylate (8.0 g, 0.0355 mol) and ethyl-2-cyanoacetate (8.03 g, 0.0710 mol) was dissolved in dioxane (250 ml). It was cooled to 0° C. To this reaction mixture, HCl gas was purged up to saturation (for 20 min, initially reaction mass becomes turbid and then becomes clears). Then reaction mass was stirred for 18 h at room temperature. After completion of the reaction it was cooled to 0° C. and basified with saturated NaHCO$_3$ (pH=8). Further it was extracted with ethyl acetate (250 ml×3). Combined organic extracts were washed with water followed with brine. Separated organic layer was dried over anhy. Na$_2$SO$_4$, filtered and concentrated to get 9 g crude product. It was purified by column chromatography by using 100-200 mesh silica gel and 1-2% MeOH: DCM solvent system to give ethyl 2-(4-hydroxy-5,6,7,8-tetrahydrobenzo[4,5]thieno[2,3-d]pyrimidin-2-yl)acetate as yellow solid. Yield—(9.0 g, 86.71%); $^1$H-NMR: (400 MHz, CDCl$_3$); δ=4.25-4.20 (q, 2H), 3.77 (s, 2H), 3.00-2.97 (m, 2H), 2.76-2.74 (m, 2H), 1.88-1.81 (m, 4H), 1.29-1.25 (t, 3H); LC-MS [M+H]=292.9.

The ethyl 2-(4-hydroxy-5,6,7,8-tetrahydrobenzo[4,5]thieno[2,3-d]pyrimidin-2-yl)acetate (9 g, 0.03078 mol) and phosphorous oxy-chloride (45 ml) was refluxed for 4 h. After completion of the reaction, it was concentrated under reduced pressure. The resulting residue was cooled to 0° C. To this, ice water (200 ml) was added and stirred for 30 min. Then it was basified with 25% aq. NH$_4$OH solution slowly to pH=8. It was extracted with DCM (250 ml×3). Organic extracts were washed with water followed by brine. The separated organic layer was dried over anhydrous Na$_2$SO$_4$ and concentrated to get crude product. It was purified by column chromatography by using 100-200 mesh silica gel and DCM as eluent to give ethyl 2-(4-chloro-5,6,7,8-tetrahydrobenzo[4,5]thieno[2,3-d]pyrimidin-2-yl)acetate as yellow liquid. Yield—(7 g, 73.16%); $^1$H-NMR: (400 MHz, CDCl$_3$); δ=4.22-4.16 (q, 2H), 4.02 (s, 2H), 3.06 (m, 2H), 2.85-2.84 (m, 2H), 1.93-1.83 (m, 4H), 1.26-1.23 (t, 3H); LC-MS [M+H]=310.9.

The ethyl 2-(4-chloro-5,6,7,8-tetrahydrobenzo[4,5]thieno[2,3-d]pyrimidin-2-yl)acetate (7.0 g, 0.0225 mol) and N-methyl cyclopropyl amine (4.8 g, 0.0675 mol) was dissolved in methanol (200 ml). To this reaction mixture, triethyl amine (13.66 g, 0.135 mol) was added slowly at room temperature. The resulting reaction mixture was stirred at room temperature for 18 h. After completion of reaction it was concentrated under reduced pressure. The residue was dissolved in DCM (250 ml) and it was washed with water. Aqueous layer was extracted with DCM (250 ml). Organic extracts were combined and washed with brine. Separated organic layer was dried over anhydrous Na$_2$SO$_4$ and concentrated to get crude compound. It was purified by column chromatography by using 100-200 mesh silica gel and 10% EtOAc:hexane as eluent to give ethyl 2-(4-(cyclopropyl(methyl)amino)-5,6,7,8-tetrahydrobenzo[4,5]thieno[2,3-d]pyrimidin-2-yl)acetate as a yellow solid. Yield—(6 g, 77.12%); $^1$H-NMR: (400 MHz, CDCl$_3$); δ=4.20-4.10 (q, 2H), 3.88 (s, 2H), 3.1 (s, 3H), 2.90-2.86 (m, 3H), 2.84-2.83 (m, 2H), 1.93-1.87 (m, 2H), 1.77-1.71 (m, 2H), 1.41 (s, 1H), 1.26-1.23 (t, 3H), 0.72-0.68 (m, 2H), 0.45-0.41 (m, 2H); LC-MS [M+H]=345.9.

The ethyl 2-(4-(cyclopropyl(methyl)amino)-5,6,7,8-tetrahydrobenzo[4,5]thieno[2,3-d]pyrimidin-2-yl)acetate (0.6 gm, 0.00173 mol) was dissolved in ethanol (2 ml) in sealed tube. To this 40% aqueous methyl amine (10 ml) was added. The resulting reaction mass was stirred for 18 h at room temperature. After completion of reaction, the solid was collected by filtration. It was washed with ethanol (2 ml) followed by hexane (5 ml) to get crude product. It was purified by column chromatography by using 100-200 mesh silica gel and 1-2% MeOH: DCM as eluent to get 2-(4-(cyclopropyl (methyl)amino)-5,6,7,8-tetrahydrobenzo[4,5]thieno[2,3-d]pyrimidin-2-yl)-N-methylacetamide as a white solid. Yield—150 mg, (32.82%); $^1$H-NMR: (400 MHz, CDCl$_3$); δ=8.17 (bs, 1H), 3.84 (s, 2H), 3.06 (s, 3H), 2.88-2.82 (m, 8H), 1.94-1.88 (m, 2H), 1.78-1.72 (m, 2H), 0.80-0.75 (m, 2H), 0.53-0.49 (m, 2H); LC-MS [M+H]=331.0; HPLC purity=99.60%.

Example 2

2-(4-(Cyclopropyl(methyl)amino)-5,6,7,8-tetrahydrobenzo[4,5]thieno[2,3-d]pyrimidin-2-yl)acetic acid (Compound 2)

To a solution of ethyl 2-(4-(cyclopropyl(methyl)amino)-5,6,7,8-tetrahydrobenzo[4,5]thieno[2,3-d]pyrimidin-2-yl)acetate (1.0 gm, 0.00289 mol) in THF (9 ml) and water (1 ml) was added lithium hydroxide hydrate (0.24 gm, 0.00578 mol). The reaction mixture was stirred at room temperature for 16 h. After completion of the reaction, it was diluted with water. The aqueous layer was made acidic to pH 1 with 2N HCl and then extracted with ethyl acetate (25 ml×3). The combined organic extracts were dried over anhydrous Na$_2$SO$_4$, filtered and concentrated to get crude compound. It was purified by column chromatography by using 100-200 mesh silica gel and 2% MeOH: DCM as eluent to get 2-(4-(cyclopropyl(methyl)amino)-5,6,7,8-tetrahydrobenzo[4,5]thieno[2,3-d]pyrimidin-2-yl)acetic acid as an off white solid. Yield: (0.4 gm, 43.57%); $^1$H-NMR: (400 MHz, DMSO-d$_6$); δ=12.46 (s, 1H), 3.70 (s, 2H), 2.99 (s, 3H), 2.96-2.91 (m, 1H), 2.90-2.87 (m, 2H), 2.83-2.80 (m, 2H), 1.88-1.84 (m, 2H), 1.71-1.66 (m, 2H), 0.78-0.65 (m, 2H), 0.43-0.31 (m, 2H); LC-MS [M+H]=317.9; HPLC purity=99.72%.

Example 3

2-(4-(Cyclopropyl(methyl)amino)-5,6,7,8-tetrahydrobenzo[4,5]thieno[2,3-d]pyrimidin-2-yl)-N,N-dimethylacetamide (Compound 3)

To 2-(4-(cyclopropyl(methyl)amino)-5,6,7,8-tetrahydrobenzo[4,5]thieno[2,3-d]pyrimidin-2-yl)acetic acid (100 mg, 0.000315 mol) in anhydrous THF (10 ml) 2M dimethyl amine in THF (0.017 g, 0.000378 mol) and HOBt (0.051 g, 0.000378 mol) were added. This mixture was cooled to 0° C. and then treated with EDC HCl (0.120 g, 0.00063 mol). The reaction mixture was allowed to warm to room temperature and kept stirred for 16 h. After completion, the reaction was diluted with water (50 ml) and extracted with ethyl acetate (25 ml×3). Combined organic extracts were washed with water (50 ml), dried over anhydrous Na$_2$SO$_4$ and concentrated under vacuum to get crude compound. It was then purified by column chromatography by using 100-200 mesh silica gel. Pure compound was eluted in 1-2% MeOH: DCM to afford 2-(4-(cyclopropyl(methyl)amino)-5,6,7,8-tetrahydrobenzo [4,5]thieno[2,3-d]pyrimidin-2-yl)-N,N-dimethylacetamide as a pale yellow oil. Yield—50 mg, (46.29%); $^1$H-NMR: (400 MHz, CDCl$_3$); δ=3.97 (s, 2H), 3.04 (s, 3H), 3.01 (s, 3H), 2.97 (s, 3H), 2.89-2.80 (m, 5H), 1.92-1.86 (m, 2H), 1.77-1.71 (m, 2H), 0.72-0.67 (m, 2H), 0.45-0.41 (m, 2H); LC-MS [M+H]=345.3; HPLC purity=98.78%.

Example 4

Cyclopropyl-(2-methoxymethyl-5,6,7,8-tetrahydrobenzo[4,5]thieno[2,3-d]pyrimidin-4-yl)-methyl-amine (Compound 4)

To a stirred mixture of 2-Amino-4,5,6,7-tetrahydro-benzo [b]thiophene-3-carboxylic acid ethyl ester (2.0 g, 0.0088 mol) and methoxyacetonitrile (1.3 ml, 0.0177 mol) in 1,4-dioxane (200 nml), dry HCl gas was purged for 30-45 minutes at 0-5° C. The reaction mixture was then warmed to room temperature and stirred for about 20 h under inert atmosphere. After completion of the reaction, the mixture was quenched with the addition of crushed ice (~200 g). The aqueous layer was then extracted well with ethyl acetate (2×250 ml). Combined organic layers was washed with brine solution (100 ml) dried over anhydrous Na$_2$SO$_4$ and concentrated under vacuum to get crude 2-Methoxymethyl-5,6,7,8-tetrahydrobenzo[4,5]thieno[2,3-d]pyrimidin-4-ol as brown colored solid which was forwarded as such for the next step. Yield: (2 g, 90%); $^1$H NMR (400 MHz, DMSO) δ ppm=12.27 (s, 1H), 4.28 (s, 2H), 3.31 (s, 3H), 2.87-2.84 (m, 2H), 2.74-2.71 (m, 2H), 1.81-1.73 (m, 4H); LCMS: [M+H]=251.1.

A stirring suspension of 2-Methoxymethyl-5,6,7,8-tetrahydro-benzo[4,5]thieno[2,3-d]pyrimidin-4-ol (2.0 g, 0.008 mol) in POCl$_3$ (20 ml) was heated to 90-95° C. for 4 h and progress was monitored by TLC. After completion of reaction, excess of POCl₃ was distilled off to get oily mass which was poured onto ice-water solution (200 ml) and basified with saturated solution of NaHCO₃ to pH ~8. The aqueous phase was extracted well with ethyl acetate (2×250 ml). Combined organic layers were washed with brine solution (100 ml), dried over anhydrous Na₂SO₄ and concentrated in vacuo to get brown colored crude compound 4-Chloro-2-methoxymethyl-5,6,7,8-tetrahydro-benzo[4,5]thieno[2,3-d]pyrimidine which was forwarded as such for the next step reaction. Yield: (2 g, 93%); $^1$H NMR (400 MHz, CDCl₃) δ ppm=4.60 (s, 2H), 3.37 (s, 3H), 3.00-2.99 (m, 2H), 2.88 (m, 2H), 1.85-1.83 (m, 4H); LCMS: [M+H]=269.1.

To a stirring suspension of compound 4-Chloro-2-methoxymethyl-5,6,7,8-tetrahydro-benzo[4,5]thieno[2,3-d]pyrimidine (1.0 g, 0.0037 mol) and cyclopropyl methylamine hydrochloride (1.18 g, 0.111 mol) in methanol (100 ml) was added TEA (3.1 ml, 0.022 mol) at 0-5° C. Reaction mixture was then warmed to room temperature and stirred for about 20 h. After completion of the reaction (monitored by TLC) volatilities were removed under vacuum and solid residue obtained was diluted with ice-water solution (200 ml). Aqueous phase was extracted with DCM (2×250 ml). Combined organic layer was washed with brine solution, dried and concentrated on rotary evaporator to get crude material which was purified by prep HPLC to get the desired title compound cyclopropyl-(2-methoxymethyl-5,6,7,8-tetrahydrobenzo[4,5]thieno[2,3-d]pyrimidin-4-yl)-methyl-amine(N-cyclopropyl-2-(methoxymethyl)-N-methyl-5,6,7,8-tetrahydrobenzo[4,5]thieno[2,3-d]pyrimidin-4-amine) as a yellow solid. Yield: (600 mg, 54.5%); 1H), 2.90-2.87 (m, 2H), 2.83-2.80 (m, 2H), 1.88-1.82 (m, 2H), 1.72-1.68 (m, 2H), 0.76 $^1$H NMR (400 MHz, DMSO) δ ppm=4.41 (s, 2H), 3.36 (s, 3H), 3.30 (s, 3H), 2.97-2.92 (m, –0.70 (m, 2H), 0.40-0.36 (m, 2H); LCMS: [M+H]=304.40; HPLC (purity): 99.61% at 236 nm, 99.45% at 220 nm, 99.32% at 254 nm.

Example 5

USP14 Inhibition Assay

Using previously described methodology [B. H. Lee et al. Nature 2010, 467 (9), 179, the contents of which are expressly incorporated by reference herein], select compounds described herein were found to inhibit USP14 as delineated in Table I. Known USP14 inhibitor IU1 (1-(1-(4-fluorophenyl)-2,5-dimethyl-1H-pyrrol-3-yl)-2-(pyrrolidin-1-yl)ethanone; B. H. Lee et al. Nature 2010, 467 (9), 179) was used as a comparative reference agent. The IC₅₀ values in the Table below represent the average value from three experimental determinations.

TABLE I

Inhibition of USP14 by Compounds in Examples 1-4.

| Compound No. | USP14 IC₅₀ (uM) |
|---|---|
| IU1 | 1.2 |
| 1 | 1.1 |
| 2 | 1.6 |
| 3 | 0.5 |
| 4 | 7.5 |

Example 6

Compounds 5 to 39

The compounds shown in the Table II below were prepared either by reaction of the amine reagent (shown in the Table below) with ethyl 2-(4-(cyclopropyl(methyl)amino)-5,6,7,8-tetrahydrobenzo[4,5]thieno[2,3-d]pyrimidin-2-yl)acetate using the procedure described in Example 1 above, or by reacting the amine reagent and coupling reagent with 2-(4-(cyclopropyl(methyl)amino)-5,6,7,8-tetrahydrobenzo[4,5]thieno[2,3-d]pyrimidin-2-yl)acetic acid using the procedure described in Example 3 above.

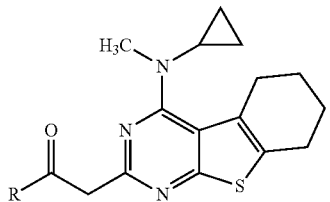

TABLE II

| Compound No. | Compound | Amine reagent | LC-MS m/z |
|---|---|---|---|
| 5 | 2-(4-(Cyclopropyl(methyl)amino)-5,6,7,8-tetrahydrobenzo[4,5]thieno[2,3-d]pyrimidin-2-yl)acetamide | 25% aqueous ammonium hydroxide | [M + H] = 317.0 |

TABLE II-continued

| Compound No. | Compound | Amine reagent | LC-MS m/z |
|---|---|---|---|
| 6 | 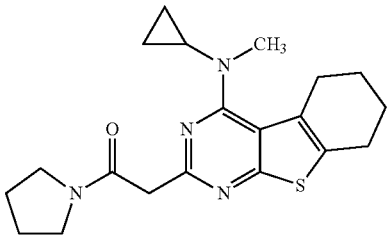 [SMILES: CN(c1nc(CC(=O)N2CCCC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-pyrrolidin-1-yl-ethanone | pyrrolidine | [M + H] = 370.9 |
| 7 | 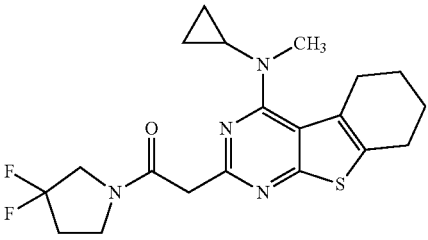 [SMILES: CN(c1nc(CC(=O)N2CCC(F)(F)C2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-(3,3-difluoro-pyrrolidin-1-yl)-ethanone | 3,3' difluoropyrrolidine HCl | [M + H] = 407.0 |
| 8 | 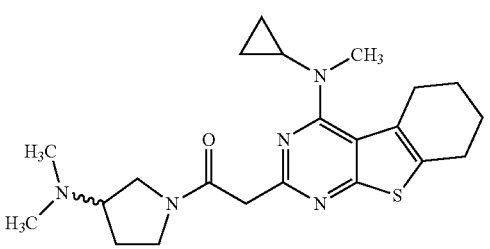<br>2-[4-(Cyclopropyl-methyl-amino)-5,6,7,8-tetrahydro-benzo[4,5]thieno[2,3-d]pyrimidin-2-yl]-1-(3-dimethylamino-pyrrolidin-1-yl)-ethanone | 3-(dimethylamino)-pyrrolidine | [M + H] = 413.9 |
| 9 | 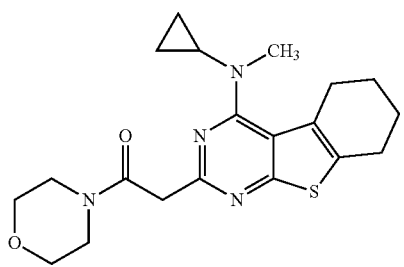 [SMILES: CN(c1nc(CC(=O)N2CCOCC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-morpholin-4-yl-ethanone | morpholine | [M + H] = 387.1 |

TABLE II-continued

| Compound No. | Compound | Amine reagent | LC-MS m/z |
|---|---|---|---|
| 10 | 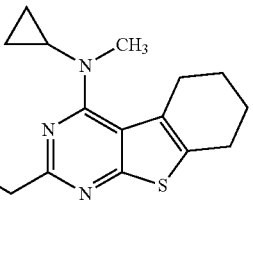 2-[4-(Cyclopropyl-methyl-amino)-5,6,7,8-tetrahydro-benzo[4,5]thieno[2,3-d]pyrimidin-2-yl]-1-(4-methyl-piperazin-1-yl)-ethanone | N-methyl piperazine | [M + H] = 399.9 |
| 11 | 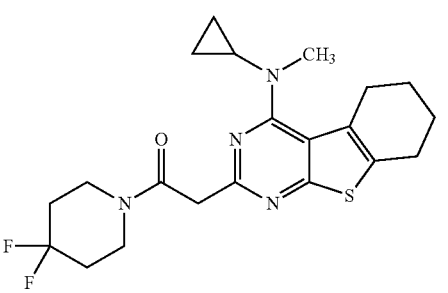 [SMILES: CN(c1nc(CC(=O)N2CCC(F)(F)CC2)nc2sc3c(c12)CCCC3)C1CC1] 2-[4-(Cyclopropyl-methyl-amino)-5,6,7,8-tetrahydro-benzo[4,5]thieno[2,3-d]pyrimidin-2-yl]-1-(4,4-difluoro-piperidin-1-yl)-ethanone | 4,4-difluoropiperidine hydrochloride | [M + H] = 421.1 |
| 12 | 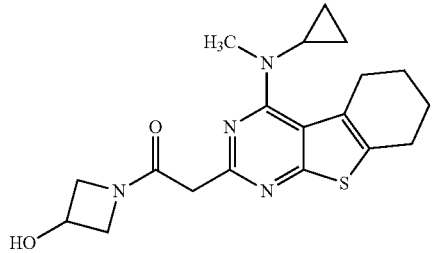 [SMILES: CN(c1nc(CC(=O)N2CC(O)C2)nc2sc3c(c12)CCCC3)C1CC1] 2-(4-(Cyclopropyl(methyl)amino)-5,6,7,8-tetrahydrobenzo[4,5]thieno[2,3-d]pyrimidin-2-yl)-1-(3-hydroxyazetidin-1-yl)ethanone | azetidin-3-ol, HCl | [M + H] = 372.98 |
| 13 | 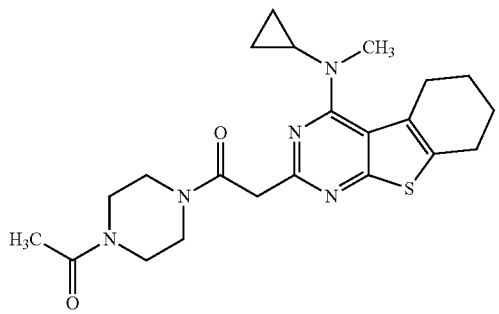 [SMILES: CC(=O)N1CCN(C(=O)Cc2nc(N(C)C3CC3)c3c4c(sc3n2)CCCC4)CC1] 1-(4-Acetyl-piperazin-1-yl)-2-[4-(Cyclopropyl-methyl-amino)-5,6,7,8-tetrahydro-[1]benzothieno[2,3-d]pyrimidin-2-yl]-ethanone | N-acetylpiperazine | [M + H] = 428.40 |

TABLE II-continued

| Compound No. | Compound | Amine reagent | LC-MS m/z |
|---|---|---|---|
| 14 | 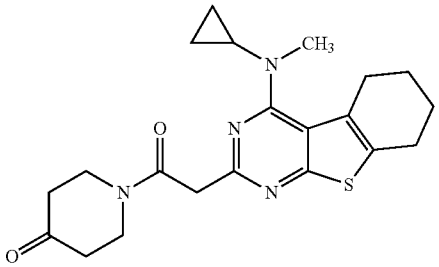 [SMILES: CN(c1nc(CC(=O)N2CCC(=O)CC2)nc2sc3c(c12)CCCC3)C1CC1] 1-{2-[4-(Cyclopropyl-methyl-amino)-5,6,7,8-tetrahydro-benzo[4,5]thieno[2,3-d]pyrimidin-2-yl]-acetyl}-piperidin-4-one | 4-piperidinone monohydrate hydrochloride | [M + H] = 398.80 |
| 15 | 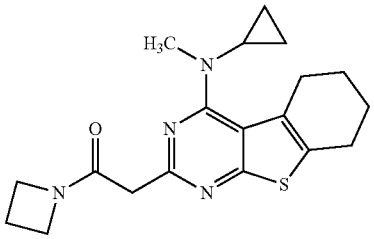 [SMILES: CN(c1nc(CC(=O)N2CCC2)nc2sc3c(c12)CCCC3)C1CC1] 1-(Azetidin-1-yl)-2-(4-(cyclopropyl(methyl)amino)-5,6,7,8-tetrahydrobenzo[4,5]thieno[2,3-d]pyrimidin-2-yl)ethanone | azetidine HCl | [M + H] = 356.99 |
| 16 | 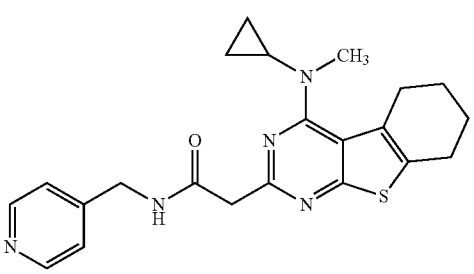 [SMILES: CN(c1nc(CC(=O)NCc2ccncc2)nc2sc3c(c12)CCCC3)C1CC1] 2-[4-(Cyclopropyl-methyl amino)-5,6,7,8-Tetrahydrobenzo(4,5)thieno(2,3-d)pyrimidin]-N-yridin-4-ylmethyl)-acetamide | 4-pyridinemethan-amine | [M + H] = 408.1 |
| 17 | 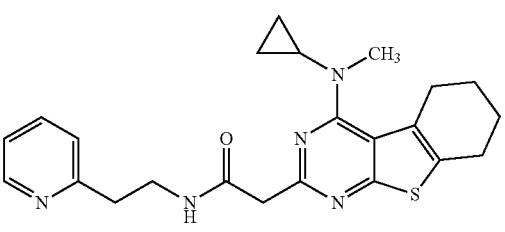 [SMILES: CN(c1nc(CC(=O)NCCc2ccccn2)nc2sc3c(c12)CCCC3)C1CC1] 2-[4-(Cyclopropyl-methylamino)-5,6,7,8-tetrahydrobenzo(4,5)thieno(2,3-d)pyrimidin]-pyrimidin-2-yl]-N-(2-pyridin-2-yl-ethyl)-acetamide | 2-pyridineethan-amine | [M + H] = 422.0 |

TABLE II-continued

| Compound No. | Compound | Amine reagent | LC-MS m/z |
| --- | --- | --- | --- |
| 18 | 2-[4-(Cyclopropyl-methyl amino)-5,6,7,8-tetrahydrobenzo(4,5)thieno(2,3-d)pyrimidin]-pyrimidin-2-yl]-N-pyridin-2-yl-methylacetamide | 2-pyridinemethanamine | [M + H] = 408.1 |
| 19 | 2-(4-(Cyclopropyl-methyl amino)-5,6,7,8-tetrahydrobenzo(4,5)thieno(2,3-d)pyrimidin)-N-yridin-2-ylmethyl)-acetamide | 3-pyridinemethanamine | [M + H] = 408.0 |
| 20 | (S)-2-(4-(Cyclopropyl(methyl)amino)-5,6,7,8-tetrahydrobenzo[4,5]thieno[2,3-d]pyrimidin-2-yl)-1-(3-(2-hydroxypropan-2-yl)pyrrolidin-1-yl)ethanone | (S)-2-(pyrrolidin-3-yl)propan-2-ol, HCl | [M + H] = 429.08 |
| 21 | 2-[4-(Cyclopropyl-methyl amino)-5,6,7,8-tetrahydrobenzo(4,5)thieno(2,3-d)pyrimidin]-2-yl]-N-(2-pyridin-4-yl-ethyl)-acetamide | 3-aminoisoxazole | [M + H] = 384.1 |

TABLE II-continued

| Compound No. | Compound | Amine reagent | LC-MS m/z |
|---|---|---|---|
| 22 | 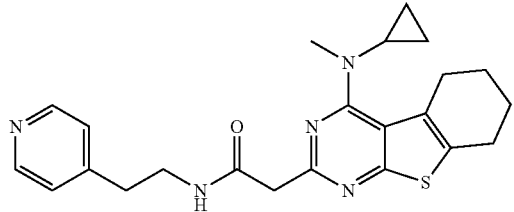 [SMILES: CN(c1nc(CC(=O)NCCc2ccncc2)nc2sc3c(c12)CCCC3)C1CC1]<br>2-[4-(Cyclopropyl-methyl amino)-5,6,7,8-tetrahydrobenzo(4,5)thieno(2,3-d)pyrimidin]-2-yl]-N-(2-pyridin-4-yl-ethyl)-acetamide | 4-pyridylethyl-amine | [M + H] = 421.9 |
| 23 | 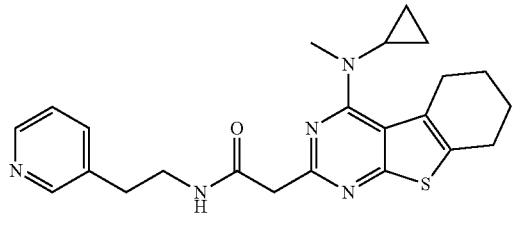 [SMILES: CN(c1nc(CC(=O)NCCc2cccnc2)nc2sc3c(c12)CCCC3)C1CC1]<br>2-[4-(Cyclopropyl-methyl amino)-5,6,7,8-tetrahydrobenzo(4,5)thieno(2,3-d)pyrimidin]-pyridin-2-yl]-N-(2-pyridin-3-yl-ethyl)-acetamide | 3-pyridylethyl-amine | [M + H] = 422.4 |
| 24 | 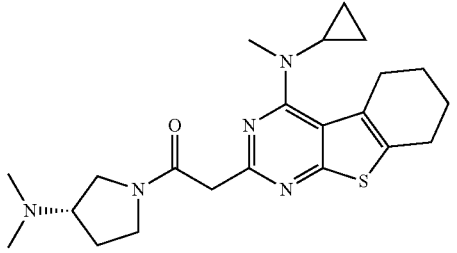 [SMILES: CN(c1nc(CC(=O)N2CC[C@H](N(C)C)C2)nc2sc3c(c12)CCCC3)C1CC1]<br>2-[4-(Cyclopropyl-methyl-amino)-5,6,7,8-tetrahydrobenzo[4,5]thieno[2,3-d]pyrimidin-2yl]-1-((s)-3-dimethylamino-pyrrolidin-1-yl)-ethanone | (S)-(−)-3-(dimethylamino)-pyrrolidine | [M + H] = 414.2 |
| 25 | 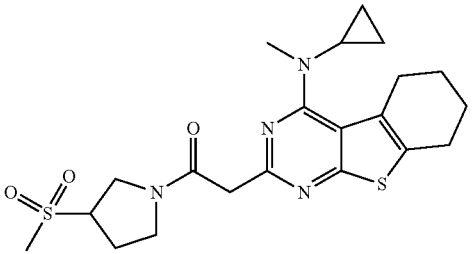 [SMILES: CN(c1nc(CC(=O)N2CCC(S(C)(=O)=O)C2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2yl]-1-(3-methanesulfonyl-pyrrolidin-1-yl)-ethanone | 3-(methylsulfonyl)pyrrolidine | [M + H] = 449.1 |

TABLE II-continued

| Compound No. | Compound | Amine reagent | LC-MS m/z |
|---|---|---|---|
| 26 | 2-[4-(Cyclopropyl-methyl-amino)-5,6,7,8-tetrahydro-benzo[4,5]thieno[2,3-d]pyrimidin-2yl]-1-piperidin-1-yl-ethanone | piperidine | [M + H] = 385.1 |
| 27 | 2-[4-(Cyclopropyl-methyl-amino)-5,6,7,8-tetrahydro-benzo[4,5]thieno[2,3-d]pyrimidin-2-yl]-1-(4-hydroxy-piperidin-1-yl)-ethanone | 4-hydroxypiperidine | [M + H] = 401.1 |
| 28 | 2-[4-(Cyclopropyl-methyl-amino)-5,6,7,8-tetrahydro-benzo[4,5]thieno[2,3-d]pyrimidin-2-yl]-N-isopropyl-acetamide | isopropylamine | [M + H] = 358.9 |
| 29 | 2-[4-(Cyclopropyl-methyl-amino)-5,6,7,8-tetrahydro-benzo[4,5]thieno[2,3-d]pyrimidin-2-yl]-1-(3-hydroxy-pyrrolidin-1-yl)-ethanone | 3-pyrrolidinol | [M + H] = 387.0 |

TABLE II-continued

| Compound No. | Compound | Amine reagent | LC-MS m/z |
|---|---|---|---|
| 30 | 2-[4-(Cyclopropyl-methyl-amino)-5,6,7,8-tetrahydro-benzo[4,5]thieno[2,3-d]pyrimidin-2-yl]-1-((R)-3-dimethylamino-pyrrolidin-1-yl)-ethanone | (R)-N,N-dimethylpyrrolidin-3-amine | [M + H] = 413.8 |
| 31 | 1-{2-[4-(Cyclopropyl-methyl-amino)-5,6,7,8-tetrahydro-benzo[4,5]thieno[2,3-d]pyrimidin-2-yl]-acetyl}-piperidine-4-carboxylic acid amide | 4-piperidinecarboxamide | [M + H] = 428.1 |
| 32 | 2-[4-(Cyclopropyl-methyl-amino)-5,6,7,8-tetrahydro-benzo[4,5]thieno[2,3-d]pyrimidin-2-yl]-1-(4-morpholin-4-yl-piperidin-1-yl)-ethanone | 4-morpholinopiperidine | [M + H] = 470.1 |
| 33 | 2-[4-(Cyclopropyl-methyl-amino)-5,6,7,8-tetrahydro-benzo[4,5]thieno[2,3-d]pyrimidin-2-yl]-1-(3-hydroxy-piperidin-1-yl)-ethanone | 3-hydroxypiperidine | [M + H] = 401.0 |

TABLE II-continued

| Compound No. | Compound | Amine reagent | LC-MS m/z |
|---|---|---|---|
| 34 | 2-[4-(Cyclopropyl-methyl-amino)-5,67,8-tetrahydro-benzo[4,5]thieno[2,3-d]pyrimidin-2-yl]-N-ethyl-acetamide | ethylamine | [M + H] = 345.3 |
| 35 | 2-[4-(Cyclopropyl-methyl-amino)-5,6,7,8-tetrahydro-benzo[4,5]thieno[2,3-d]pyrimidin-2-yl]-N-(3-hydroxy-3-methyl-butyl)-acetamide | 4-amino-2-methylbutan-2-ol | [M + H] = 402.8 |
| 36 | 2-[4-(Cyclopropyl-methyl-amino)-5,6,7,8-tetrahydro-benzo[4,5]thieno[2,3-d]pyrimidin-2-yl]-1-(3-hydroxymethyl-pyrrolidin-1-yl)-ethanone | 3-(hydroxymethyl)pyrrolidine | [M + H] = 401.1 |
| 37 | 2-[4-(Cyclopropyl-methyl-amino)-5,6,7,8-tetrahydro-benzo[4,5]thieno[2,3-d]pyrimidin-2-yl]-1-[(R)-3-(1-hydroxy-1-methyl-ethyl)-pyrrolidin-1-yl]-ethanone | (R)-2-(3-pyrrolidinyl)-2-propanol | [M + H] = 428.8 |

TABLE II-continued

| Compound No. | Compound | Amine reagent | LC-MS m/z |
|---|---|---|---|
| 38 | 1-(2-(4-(Cyclopropyl(methyl)amino)-5,6,7,8-tetrahydrobenzo[4,5]thieno[2,3-d]pyrimidin-2-yl)acetyl)pyrrolidine-2-carboxamide | 2-pyrrolidine-carboxamide | [M + H] = 413.8 |
| 39 | 2-[4-(Cyclopropyl-methyl-amino)-5,6,7,8-tetrahydro-benzo[4,5]thieno[2,3-d]pyrimidin-2-yl]-1-(2-hydroxymethyl-pyrrolidin-1-yl)-ethanone. | 2-hydroxymethyl-pyrrolidine | [M + H] = 400.7 |

Example 7

Compounds 40 to 46

The compounds shown in the Table III below were prepared from (4-chloro-5,6,7,8-tetrahydro-benzo[4,5]thieno[2,3-d]pyrimidin-2-yl)-acetic acid ethyl ester using methods similar to those described in Examples 1 to 3.

TABLE III

| | Compound | LC-MS m/z |
|---|---|---|
| 40 | [4-(Ethyl-methyl-amino)-5,6,7,8-tetrahydro-benzo[4,5]thieno[2,3-d]pyrimidin-2-yl]-acetic acid ethyl ester | [M + H] = 333.9 |
| 41 | [4-(Isopropyl-methyl-amino)-5,6,7,8-tetrahydro-benzo[4,5]thieno[2,3-d]pyrimidin-2-yl]-acetic acid ethyl ester | [M + H] = 347.8 |
| 42 | N,N-Dimethyl-2-(4-pyrrolidin-1-yl-5,6,7,8-tetrahydro-benzo[4,5]thieno[2,3-d]pyrimidin-2-yl)-acetamide | [M + H] = 345.3 |

TABLE III-continued

| Compound | LC-MS m/z |
|---|---|
| 43  2-(4-Dimethylamino-5,6,7,8-tetrahydro-benzo[4,5]thieno[2,3-d]pyrimidin-2-yl)-N,N-dimethyl-acetamide | [M + H] = 319.0 |
| 44  2-(4-(Azetidin-1-yl)-5,6,7,8-tetrahydrobenzo[4,5]thieno[2,3-d]pyrimidin-2-yl)-N,N-dimethylacetamide | [M + H] = 331.0 |
| 45  [4-(Ethyl-methyl-amino)-5,6,7,8-tetrahydro-benzo[4,5]thieno[2,3-d]pyrimidin-2-yl]-acetic acid | [M + H] = 306.0 |
| 46  [4-(Isopropyl-methyl-amino)-5,6,7,8-tetrahydro-benzo[4,5]thieno[2,3-d]pyrimidin-2-yl]-acetic acid. | [M + H] = 320.0 |

Example 8

3-[4-(Cyclopropyl-methyl-amino)-5,6,7,8-tetrahydro-[1]benzothiopheno[2,3-d]pyrimidin-2-yl]-propionic acid (Compound 47)

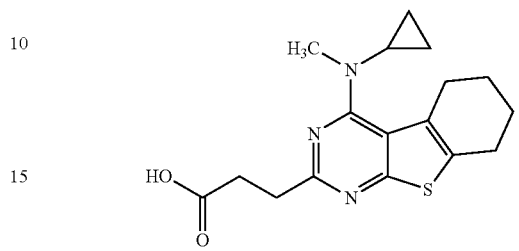

Monomethyl hydrogen succinate (4.7 g, 0.035 mol) was refluxed in thionyl chloride (20 ml) for 2 hrs. After consumption of starting material, excess of thionyl chloride was distilled off. The reaction mixture dissolved in dioxane (10 ml) and was added drop wise to 2-amino-4,5,6,7-tetrahydro-1-benzothiophene-3-carboxamide 1 (7 g, 0.035 moles) in dioxane (10 ml) at 0° C. and stirred at room temperature (R.T) for 2 hrs. The reaction mixture was diluted with water to give crude product which was filtered and washed with water. The crude was purified by chromatography on silica gel using 1:1 Ethyl acetate:Hexane to give 5 g (46%) of N-(3-carbonyl-4,5,6,7-tetrahydro-benzo[b]thiophen-2-yl)-succinamic acid methyl ester. $^1$H NMR (400 MHz, DMSO) δ ppm=1.72 (m, 4H), 2.6 (m, 4H), 2.68 (m, 4H), 3.59 (s, 3H), 6.99 (s, 1H), 7.55 (s, 1H), 11.48 (s, 1H). LC-MS: [M−H]=308.9.

The N-(3-carbonyl-4,5,6,7-tetrahydro-benzo[b]thiophen-2-yl)-succinamic acid methyl ester (5 g, 0.016 mol) was refluxed in 2N sodium hydroxide solution (100 ml) for 1.5 hr. After consumption of starting material, the reaction mixture was cooled, and acidified (pH 5) with ice cold diluted hydrochloric acid; the resulting solid was filtered, washed with water followed by ether, and dried to give the crude 3-(4-hydroxy-5,6,7,8-tetrahydro-[1]benzothiopheno[2,3-d]pyrimidin-2-yl)-propionic acid (3 g (68%) which was used without further purification. $^1$H NMR (400 MHz, DMSO) δ ppm=1.75 (m, 4H), 2.67 (m, 4H), 2.83 (m, 4H), 12.24 (s, 1H). LC-MS: [M+H]=279.1.

To a solution of 3-(4-hydroxy-5,6,7,8-tetrahydro-[1]benzothiopheno[2,3-d]pyrimidin-2-yl)-propionic acid (3 g, 0.01 mol) in methanol (15 ml) was added catalytic amount of sulphuric acid (0.2 ml) and the solution was refluxed for 2 hrs. The methanol was distilled off, and the residue was washed with sodium bicarbonate solution to give 2 g (63%) of 3-(4-hydroxy-5,6,7,8-tetrahydro-[1]benzothiopheno[2,3-d]pyrimidin-2-yl)-propionic acid methyl ester as an off-white solid, which was used without further purification. $^1$H NMR (400 MHz, DMSO) δ ppm=1.73 (m, 4H), 2.6 (m, 2H), 2.78 (m, 2H), 2.83 (m, 4H), 3.37 (s, 3H), 12.18 (s, 1H). LC-MS: [M+H]=293.3.

A solution of 3-(4-hydroxy-5,6,7,8-tetrahydro-[1]benzothiopheno[2,3-d]pyrimidin-2-yl)-propionic acid methyl ester (2 g, 0.0068 mol) in POCl3 (10 ml) was refluxed for 2 hrs. After consumption of starting material, excess of POCl3 was distilled off. The reaction mixture was quenched with ice and extracted with ethyl acetate (3×25 ml). The combined organic layers were dried over Na$_2$SO$_4$, concentrated and purified by chromatography on 60-120 silica using ethyl acetate (30%) in hexane as eluant to give 1 g (47%) of 3-(4- chloro-5,6,7,8-tetrahydro-[1]benzothiopheno[2,3-d]pyrimidin-2-yl)-propionic acid methyl ester. ¹H NMR (400 MHz, DMSO) δ ppm=1.83 (m, 4H), 2.8 (m, 4H), 2.98 (m, 2H), 3.2 (t, 2H), 3.57 (s, 3H). LC-MS: [M+H]=311.1.

The TEA (0.6 g, 0.0064 mol) was added dropwise at 10° C. to a mixture of 3-(4-chloro-5,6,7,8-tetrahydro-[1]benzothiopheno[2,3-d]pyrimidin-2-yl)-propionic acid methyl ester (1 g, 0.0032 mol) and cyclopropyl methyl amine hydrochloride (0.35 g, 0.0032 mol) in methanol (20 ml). The resulting mixture was stirred at R.T for 10 hrs. Methanol was removed and the reaction mixture was diluted with water and extracted with ethyl acetate (3×25 ml). The combined organic layers were dried over $Na_2SO_4$, concentrated and subjected to column purification on 60-120 silica using ethyl acetate (50%) in hexane to give 0.5 g (43%) of 3-[4-(cyclopropyl-methyl-amino)-5,6,7,8-tetrahydro-[1]benzothiopheno[2,3-d]pyrimidin-2-yl]-propionic acid methyl ester. ¹H NMR (400 MHz, DMSO) δ ppm=0.35 (m, 2H), 0.72 (m, 2H), 1.69 (m, 2H), 1.85 (m, 2H), 2.77 (q, 4H), 2.86 (q, 2H), 2.9 (m, 1H), 2.97 (s, 3H) 3.02 (t, 2H), 3.56 (s, 3H). LC-MS: [M+H]=345.8.

The LiOH (0.047 g, 0.0018 mol) dissolved in water (2 ml) was added to a solution of 3-[4-(cyclopropyl-methyl-amino)-5,6,7,8-tetrahydro-[1]benzothiopheno[2,3-d]pyrimidin-2-yl]-propionic acid methyl ester (0.5 g, 0.0014 mol) in THF (3 ml), and the resulting solution was stirred at R.T for 3 hrs. The reaction mixture was diluted with water, acidified with dilute HCl (up to pH 5) and extracted with ethyl acetate (3×15 ml). The combined organic layers were dried over $Na_2SO_4$, concentrated, and the crude was purified by preparative HPLC to give 0.25 g (54%) of 3-[4-(cyclopropyl-methyl-amino)-5,6,7,8-tetrahydro-[1]benzothiopheno[2,3-d]pyrimidin-2-yl]-propionic acid. ¹H NMR (400 MHz, CDCl₃) δ ppm=0.53 (m, 2H), 0.87 (m, 2H), 1.76 (m, 2H), 1.92 (m, 2H), 2.84 (m, 7H), 3.1 (s, 3H), 3.22 (t, 2H), 14.75 (s, 1H). LC-MS: [M+H]=331.9.

Example 9

3-[4-(Cyclopropyl-methyl-amino)-5,6,7,8-tetrahydro-[1]benzothiopheno[2,3-d]pyrimidin-2-yl]-N,N-dimethyl-propionamide (Compound 48)

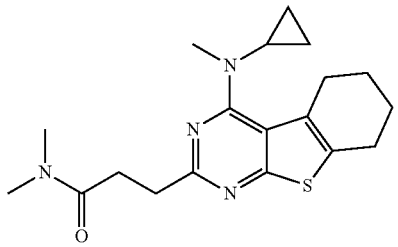 [SMILES: CN(C)C(=O)CCc1nc(N(C)C2CC2)c2c3c(sc2n1)CCCC3]

To a mixture of 3-[4-(cyclopropyl-methyl-amino)-5,6,7,8-tetrahydro-[1]benzothiopheno[2,3-d]pyrimidin-2-yl]-propionic acid (0.2 g, 0.0006 mol) and EDC HCl (0.116 g, 0.0006 mol) in THF (10 ml) was added triethyl amine (0.122 g, 0.0012 mol), and the resulting mixture was stirred at R.T for 15 min. The dimethyl amine (0.0027 g, 0.0006 mol) in THF was added dropwise to the reaction mixture and stirring at R.T was continued for another 4 hrs. The solvent was removed; the reaction mixture was diluted with water and extracted with ethyl acetate (3×10 ml). The combined organic layers were dried over $Na_2SO_4$, concentrated. The crude material was subjected to column purification on 60-120 silica using ethyl acetate (50%) in hexane to give 0.05 g (51%) of the desired product as off-white solid. ¹H NMR (400 MHz, CDCl₃) δ ppm=0.43 (m, 2H), 0.69 (m, 2H), 1.75 (m, 2H), 1.89 (m, 2H), 2.85 (m, 7H), 2.94 (s, 3H), 3.0 (s, 3H), 3.05 (s, 3H), 3.20 (t, 2H). LC-MS: [M+H]=359.3.

Example 10

[4-(Cyclopropyl-methyl-amino)-5,6,7,8-tetrahydrobenzo[4,5]thieno[2,3-d]pyrimidin-2-yl]-methanol (Compound 49)

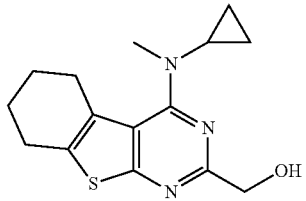 [SMILES: CN(c1nc(CO)nc2sc3c(c12)CCCC3)C1CC1]

To a mixture of 2-amino-4,5,6,7-tetrahydro-1-benzothiophene-3-carboxamide (30 g, 0.153 mol) and triethylamine (18.5 g, 0.183 mol) in DCM (200 ml) was added chloro-acetyl chloride (20.57 g, 0.183 mol) slowly at 0° C., and the resulting mixture was stirred at room temperature for 2 h. The reaction mixture was concentrated to half of the volume to afford the solid product which was filtered, washed with 10 ml of DCM and dried to provide 2-(2-chloro-acetylamino)-4,5,6,7-tetrahydro-benzo[b]thiophene-3-carboxylic acid amide (35 g, 84%) as off-white solid. ¹H NMR (400 MHz, DMSO-d₆): δ 1.65-1.75 (m, 4H), 2.58-2.72 (m, 4H), 4.49 (s, 2H), 7.29 (s, 1H), 7.42 (s, 1H), 12.23 (s, 1H); LC-MS: [M+H]=272.8, 275.1, 257.9 & 255.9 m/z.

The 2-(2-chloro-acetylamino)-4,5,6,7-tetrahydro-benzo[b]thiophene-3-carboxylic acid amide (20 g, 0.073 mol) in 150 ml of 1.5M-NaOH solution was refluxed for 4 h. The reaction mixture was cooled and filtered. The filtrate was acidified (pH=5) with dilute hydrochloric acid to give solid material. The solid was filtered, washed with water, and dried to provide 2-hydroxymethyl-5,6,7,8-tetrahydrobenzo[4,5]thieno[2,3-d]pyrimidin-4-ol (4.5 g, 25%) as yellow solid. ¹H NMR (400 MHz, DMSO-d₆): δ 1.70-1.80 (m, 4H), 2.68-2.75 (m, 2H), 2.80-2.88 (m, 2H), 4.35 (d, 2H), 5.61 (t, 1H), 11.95 (s, 1H); LC-MS: [M+H]=237.2 m/z.

The 2-hydroxymethyl-5,6,7,8-tetrahydrobenzo[4,5]thieno[2,3-d]pyrimidin-4-ol (4.5 g, 0.019 mol) in 10 ml of acetic anhydride was treated with triethylamine (3.8 g, 0.038 mol) at 0° C., and the mixture was stirred at room temperature for 2 h. The reaction mixture was poured into water and the resulting solid was filtered, washed with water & hexanes, and dried to provide acetic acid 4-hydroxy-5,6,7,8-tetrahydrobenzo[4,5]thieno[2,3-d]pyrimidin-2-ylmethyl ester (4 g, 75%) as yellow solid. ¹H NMR (400 MHz, CDCl₃): δ 1.74-1.90 (m, 4H), 2.21 (s, 3H), 2.70-2.80 (m, 2H), 2.95-3.02 (m, 2H), 5.07 (s, 2H), 10.52 (brs, 1H); LC-MS: [M+H]=279.1 m/z.

The acetic acid 4-hydroxy-5,6,7,8-tetrahydrobenzo[4,5]thieno[2,3-d]pyrimidin-2-ylmethyl ester (4 g, 0.014 mol) in 20 ml of POCl₃ was refluxed for 2 h. The excess of POCl₃ was distilled off; the reaction mixture was quenched with ice, and extracted with ethyl acetate (3×25 ml). The combined organic layers were washed with bicarbonate solution, dried over anhydrous sodium sulphate, concentrated and dried to give acetic acid 4-chloro-5,6,7,8-tetrahydro-benzo[4,5]thieno[2,3-d]pyrimidin-2-ylmethyl ester (3.5 g, 85%) as brown solid.

¹H NMR (400 MHz, CDCl₃): δ 1.85-1.95 (m, 4H), 2.20 (s, 3H), 2.84-2.90 (m, 2H), 3.04-3.10 (m, 2H), 5.30 (s, 2H); LC-MS: [M+H]=297.2 & 299.1 m/z.

A mixture of acetic acid 4-chloro-5,6,7,8-tetrahydrobenzo[4,5]thieno[2,3-d]pyrimidin-2-ylmethyl ester (3.5 g, 0.011 mol), cyclopropylmethylamine hydrochloride (2.5 g, 0.023 mol) and triethylamine (4.6 g, 0.046 mol) in acetonitrile (15 ml) was stirred at room temperature for 12 h. The solvent was removed by distillation, and the residue was diluted with water and extracted with ethyl acetate (3×25 ml). The combined organic layers were dried over anhydrous sodium sulphate, concentrated to give acetic acid 4-(cyclopropyl-methyl-amino)-5,6,7,8-tetrahydro-benzo[4,5]thieno[2,3-d]pyrimidin-2-ylmethyl ester (3.5 g, 89%) as brown solid. ¹H NMR (400 MHz, CDCl₃): δ 0.43-0.47 (m, 2H), 0.69-0.77 (m, 2H), 1.71-1.77 (m, 2H), 1.87-1.93 (m, 2H), 2.18 (s, 3H), 2.82-2.92 (m, 5H), 3.03 (s, 3H), 5.19 (s, 2H); LC-MS: [M+H]=331.8 m/z.

To a solution of acetic acid 4-(cyclopropyl-methyl-amino)-5,6,7,8-tetrahydro-benzo[4,5]thieno[2,3-d]pyrimidin-2-ylmethyl ester (4 g, 0.012 mol) in THF (10 ml) and water (5 ml) was added lithium hydroxide monohydrate (1.48 g, 0.036 mol). The solution stirred at room temperature for 4 h. The volatiles were removed by distillation, and the residue was diluted with water, and extracted with ethyl acetate (3×25 ml). The combined organic layers were dried over anhydrous sodium sulphate, concentrated, and purified by chromatography on 60-120 silica gel using 25%-ethyl acetate in hexane to give the desired product [4-(cyclopropyl-methyl-amino)-5,6,7,8-tetrahydro-benzo[4,5]thieno[2,3-d]pyrimidin-2-yl]-methanol (2.5 g, 72%) as off-white solid. ¹H NMR (400 MHz, CDCl₃): δ 0.45-0.50 (m, 2H), 0.72-0.80 (m, 2H), 1.72-1.80 (m, 2H), 1.88-1.94 (m, 2H), 2.82-2.94 (m, 5H), 3.07 (s, 3H), 3.94 (t, 1H), 4.70 (d, 2H); LC-MS: [M+H]=290.0 m/z.

Example 11

Cyclopropyl-methyl-[2-(pyridine-3-yloxymethyl)-5,6,7,8-tetrahydro-benzo[4,5]thieno[2,3-d]pyrimidin-4-yl]-amine (Compound 50)

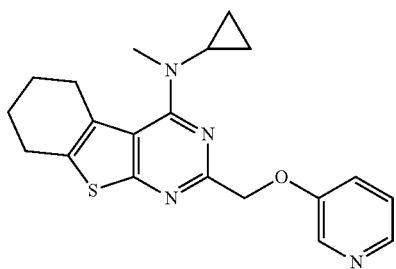 [SMILES: CN(c1nc(COc2cccnc2)nc2sc3c(c12)CCCC3)C1CC1]

To a mixture of [4-(cyclopropyl-methyl-amino)-5,6,7,8-tetrahydro-benzo[4,5]thieno[2,3-d]pyrimidin-2-yl]-methanol (0.25 g, 0.00086 mol), 3-hydroxypyridine (0.090 g, 0.00095 mol) & triphenylphosphine (0.24 g, 0.00095 mol) in THF (20 ml) was added DIAD (0.19 g, 0.00095 mol) in THF (5 ml), and the mixture was stirred at room temperature for 12 h. The reaction mixture was concentrated and the resulting crude material was purified by preparative HPLC to give cyclopropyl-methyl-[2-(pyridine-3-yloxymethyl)-5,6,7,8-tetrahydro-benzo[4,5]thieno[2,3-d]pyrimidin-4-yl]-amine (35 mg, 11%) as a brown residue. ¹H NMR (400 MHz, CDCl₃): δ 0.35-0.42 (m, 2H), 0.62-0.68 (m, 2H), 1.72-1.78 (m, 2H), 1.88-1.97 (m, 2H), 2.80-2.90 (m, 5H), 3.00 (s, 3H), 5.24 (s, 2H), 7.16 (dd, 1H), 7.30 (dd, 1H), 8.17 (dd, 1H), 8.42 (d, 1H); LC-MS: [M+H]=367.3 m/z.

Example 12

3-[4-(Cyclopropyl-methyl-amino)-5,6,7,8-tetrahydrobenzo[4,5]thieno[2,3-d]pyrimidin-2-yl]-1,1,1-trifluoro-propan-2-one (Compound 51)

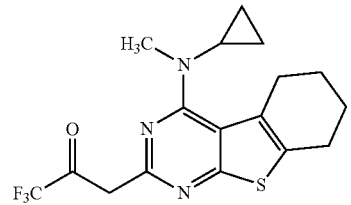 [SMILES: CN(c1nc(CC(=O)C(F)(F)F)nc2sc3c(c12)CCCC3)C1CC1]

The n-BuLi (0.504 g, 0.0078 mol) in hexane was added drop wise (under N₂ at −78° C.) to a stirred solution of dry DIPA (0.79 g, 0.0078 mol) in dry THF (40 mL), and the solution was stirred for 30 minutes, then warmed to 0° C. and stirred for one hr. The solution of LDA was cooled to −78° C. and a solution of 2-(4-(cyclopropyl(methyl)amino)-5,6,7,8-tetrahydrobenzo[4,5]thieno[2,3-d]pyrimidin-2-yl)acetic acid (1.0 g, 0.00315 mol) in dry THF was added drop wise, and the mixture was stirred at −78° C. for two hr, then at 0° C. for 30 minutes.

The solution was cooled to −78° C. and ethyl trifluoroacetate (1.341 g, 0.0094 mol) was added drop wise, and the mixture was stirred for 45 minutes. The reaction was quenched with dilute HCl at −78° C. and extracted in ethyl acetate (3×30 mL). The organic layers were combined, washed with water (50 ml) and brine solution (50 ml), dried over sodium sulphate and concentrated. The crude was isolated from acetonitrile to give 0.346 g (29.82%) of the desired product as a pale yellow colored solid. ¹H NMR (400 MHz, CDCl₃): δ ppm=14.96 (s, 1H), 6.10 (s, 1H), 3.14 (s, 3H), 2.87-2.81 (m, 5H), 1.93-1.91 (m, 2H), 1.77-1.74 (q, 2H), 0.91-0.89 (d, 2H), 0.59 (bs, 2H), LC-MS: [M+H]: 369.8.

Example 13

[4-(Cyclopropyl-methyl-amino)-6,7,8,9-tetrahydro-5H-10-thia-1,3-diazabenz[a]azulen-2-yl]-acetic acid (Compound 52)

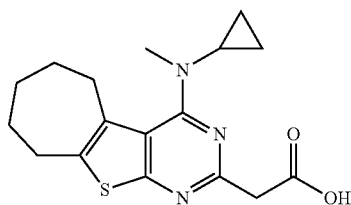 [SMILES: CN(c1nc(CC(=O)O)nc2sc3c(c12)CCCCC3)C1CC1]

Ethyl cyanoacetate (10 g, 0.089 mol), sulfur (2.85 g, 0.089 mol) and diethylamine (9.24 ml, 0.089 mol) were added to a solution of cycloheptanone (10 g, 0.089 mol) in 100 ml of ethanol and the solution was stirred for 18 h at ambient temperature. The ethanol was removed under vacuum and the crude was purified by chromatography on silica gel using 5-10% ethyl acetate in hexanes to give 2-amino-5,6,7,8-tetrahydro-4H-cyclohepta[b]thiophene-3-carboxylic acid ethyl ester (7 g, 33%) as pale yellow solid. $^1$H NMR (400 MHz, CDCl$_3$): δ 5.74 (brs, 2H), 4.26 (q, 2H), 2.90-2.98 (m, 2H), 2.52-2.58 (m, 2H), 1.72-1.86 (m, 2H), 1.55-1.65 (m, 4H), 1.33 (t, 3H); LC-MS: [M+H]=240.3 & 194.0 m/z.

A mixture of 2-amino-5,6,7,8-tetrahydro-4H-cyclohepta[b]thiophene-3-carboxylic acid ethyl ester (7 g, 0.02928 mol) and ethyl cyanoacetate (6.5 g, 0.05857 mol) in 72 ml of 1,4-dioxane was saturated with HCl gas while cooling the mixture. The mixture was stirred for 18 h at ambient temperature, then quenched with solid NaHCO$_3$, diluted with 100 ml water and extracted with ethyl acetate (100 ml×3). The organic layer was separated, dried over Na$_2$SO$_4$ and concentrated under vacuum. The crude solid was triturated with diethyl ether (100 ml) to give (4-hydroxy-6,7,8,9-tetrahydro-5H-10-thia-1,3-diaza-benz[a]azulen-2-yl)-acetic acid ethyl ester (5.5 g, 62%) as a pale yellow solid. $^1$H NMR (400 MHz, CDCl$_3$): δ 11.84 (brs, 1H), 4.18-4.28 (m, 2H), 3.78 (s, 2H), 3.22-3.32 (m, 2H), 2.80-2.90 (m, 2H), 1.83-1.93 (m, 2H), 1.58-1.75 (m, 5H), 1.26 (t, 3H); LC-MS: [M+H]=307.1 m/z.

The POCl$_3$ (20 ml, 215 mmol)) was added to (4-hydroxy-6,7,8,9-tetrahydro-5H-10-thia-1,3-diaza-benz[a]azulen-2-yl)-acetic acid ethyl ester (5.5 g, 0.01795 mol) and the solution was refluxed for 2 h. The reaction was quenched into 200 g of ice and extracted with 3×100 ml ethyl acetate. The combined organic layers were dried over sodium sulphate and concentrated under vacuum. The crude was purified by chromatography on silica gel using 10% ethyl acetate in hexanes to give (4-chloro-6,7,8,9-tetrahydro-5H-10-thia-1,3-diazabenz[a]azulen-2-yl)-acetic acid ethyl ester (2 g, 34%) as a pale yellow solid. $^1$H NMR (400 MHz, CDCl$_3$): δ 4.19 (q, 2H), 4.02 (s, 2H), 3.30-3.37 (m, 2H), 2.92-2.98 (m, 2H), 1.85-1.95 (m, 2H), 1.65-1.78 (m, 4H), 1.25 (t, 3H); LC-MS: [M+H]=325.0 & 327.1 m/z.

Cyclopropyl-methyl amine HCl (1.32 g, 0.0123 mol) and Et$_3$N (2.4 g, 0.0246 mol) were added to a solution of (4-chloro-6,7,8,9-tetrahydro-5H-10-thia-1,3-diaza-benz[a]azulen-2-yl)-acetic acid ethyl ester (2 g, 0.00615 mol) in 20 ml of methanol and the mixture was stirred for 18 h at ambient temperature. The methanol was removed under vacuum and the crude was purified by chromatography on silica gel using 10% ethyl acetate in hexanes to give [4-(cyclopropyl-methyl-amino)-6,7,8,9-tetrahydro-5H-10-thia-1,3-diaza-benz[a]azulen-2-yl]-acetic acid ethyl ester (1.8 g, 81%) as a pale yellow liquid. $^1$H NMR (400 MHz, CDCl$_3$): δ 4.18 (q, 2H), 3.89 (s, 2H), 2.92-3.00 (m, 5H), 2.78-2.90 (m, 3H), 1.85-1.92 (m, 2H), 1.68-1.77 (m, 2H), 1.60-1.67 (m, 2H), 1.25 (t, 3H), 0.68-0.75 (m, 2H), 0.40-0.47 (m, 2H); LC-MS: [M+H]:=359.9 m/z.

The LiOH (0.615 g, 0.0150 mol) was added to a solution of [4-(cyclopropyl-methyl-amino)-6,7,8,9-tetrahydro-5H-10-thia-1,3-diaza-benz[a]azulen-2-yl]-acetic acid ethyl ester (1.8 g, 0.0050 mol) in 20 ml of (5:1) THF:water, and the mixture was stirred for 18 h at ambient temperature. The solvent was reduced under vacuum and the residue was diluted with 50 ml dilute aqueous HCl. The mixture was extracted with dichloromethane (50 ml×3) and the combined organic phase was separated, dried over Na$_2$SO$_4$ and concentrated under vacuum. The crude was purified by chromatography on silica gel using 2% MeOH-DCM to give [4-(cyclopropyl-methyl-amino)-6,7,8,9-tetrahydro-5H-10-thia-1,3-diazabenz[a]azulen-2-yl]-acetic acid (1.5 g, 94%) as pale yellow oil. $^1$H NMR (400 MHz, CDCl$_3$): δ 15.52 (brs, 1H), 3.96 (s, 2H), 3.09 (s, 3H), 2.85-2.98 (m, 4H), 2.72-2.80 (m, 1H), 1.85-1.95 (m, 2H), 1.68-1.78 (m, 2H), 1.85-1.67 (m, 2H), 0.88-0.98 (m, 2H), 0.52-0.67 (m, 2H); LC-MS: [M+H]=332.2 m/z.

Example 14

2-[4-(Cyclopropyl-methyl-amino)-6,7,8,9-tetrahydro-5H-10-thia-1,3-diaza-benz[a]azulen-2-yl]-N,N-dimethyl-acetamide (Compound 53)

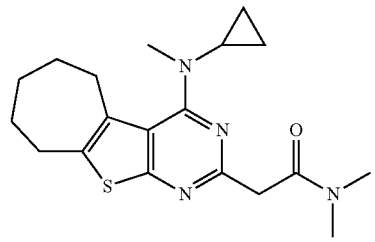 [SMILES: CN(C)C(=O)Cc1nc(N(C)C2CC2)c2c3c(sc2n1)CCCCC3]

The EDCI (0.477 g, 0.00241 mol), HOBt (0.22 g, 0.00144 mol) and N,N-dimethyl amine in THF (2 M, 1.2 ml, 0.00241 mol) were added to a solution of [4-(cyclopropyl-methyl-amino)-6,7,8,9-tetrahydro-5H-10-thia-1,3-diazabenz[a]azulen-2-yl]-acetic acid (0.4 g, 0.0012 mol) in 10 ml of THF. The mixture was stirred for 3 h at room temperature then concentrated under vacuum. The crude was purified by chromatography on silica gel using 2% MeOH-DCM to give 2-[4-(cyclopropyl-methyl-amino)-6,7,8,9-tetrahydro-5H-10-thia-1,3-diaza-benz[a]azulen-2-yl]-N,N-dimethyl-acetamide (0.25 g, 58%) as pale yellow oil. $^1$H NMR (400 MHz, CDCl$_3$): δ 3.98 (s, 2H), 3.06 (s, 3H), 2.92-3.02 (m, 8H), 2.84-2.88 (m, 2H), 2.72-2.83 (m, 1H), 1.82-1.90 (m, 2H), 1.67-1.78 (m, 2H), 1.50-1.60 (m, 2H), 0.62-0.72 (m, 2H), 0.40-0.48 (m, 2H); LC-MS: [M+H]=359.4 m/z.

Example 15

USP14 Inhibition Assay of Compounds 5 to 53

Using the methods described above in Example 6, select compounds described herein were found to inhibit USP14 as described as follows. Compounds 5, 6, 8, 9, 10, 12, 13, 14, 15, 20, 24, 25, 27, 29, 30, 31, 32, 33, 36, 37, 38, and 39 had an IC$_{50}$ of less than 1 uM. Compounds 7, 11, 16, 17, 18, 19, 21, 23, 26, 28, 34, 35, 43, 47, 48, 49, 51 and 53 had an IC$_{50}$ of between 1 and 5 uM. Compounds 22, 40, 41, 42, 44, 45, 46, 50 and 52 had an IC$_{50}$ of greater than 5 uM. These IC$_{50}$ values represent the average value from three experimental determinations.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the Formula (I):

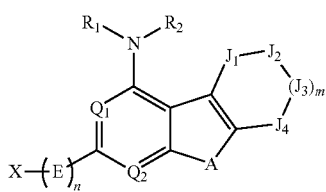

or a pharmaceutically acceptable salt thereof; wherein:

$Q_1$ and $Q_2$ are each nitrogen;

A is sulfur;

$R_1$ is $C_1$-$C_4$ alkyl;

$R_2$ is $C_3$-$C_6$ cycloalkyl;

X is selected from the group consisting of $OR_3$, $C(O)R_3$, $C(O)OR_3$, $OC(O)R_3$, $C(O)NR_aR_b$, $C(O)NR_aS(O)_2R_3$, $S(O)_2NR_aR_b$, $S(O)NR_aR_b$, $NR_aS(O)_2R_3$, CN, $SR_3$, $S(O)R_3$, $S(O)_2R_3$, $P(O)(OR_3)_2$, $NR_aR_b$, $N(R_a)OR_3$, $NR_aC(O)C(O)R_3$, $NR_aC(O)R_3$, $NR_aC(O)NR_aR_b$ and $NR_aS(O)_2NR_aR_b$;

$R_3$ is selected from the group consisting of hydrogen, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, heterocyclic, aryl and 5- to 10-membered heteroaryl; wherein the $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, heterocyclic, aryl, and heteroaryl are each optionally substituted with one or more substituents independently selected from the group consisting of halo, —$C_1$-$C_{12}$ alkyl, —$C_2$-$C_{12}$ alkenyl, —$C_2$-$C_{12}$ alkynyl, OH, $OR_x$, $NH_2$, $NHR_x$, $N(R_x)_2$, $C(O)NH_2$, $C(O)N(R_x)_2$, oxo, halo-$C_1$-$Cl_2$ alkyl, $C_1$-$C_{12}$ alkyl substituted with OH or $OR_x$, 5- to 10-membered heteroaryl, 3- to 10-membered heterocyclic, $SO_2H$, and $SO_2(C_1$-$C_{12}$ alkyl); wherein $R_x$ is $C_1$-$C_{12}$ alkyl;

$R_a$ and $R_b$ are each independently selected from the group consisting of hydrogen, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, 3-10 membered heterocyclic, aryl and 5- to 10-membered heteroaryl; alternatively, $R_a$ and $R_b$ are taken together with the nitrogen atom to which they are attached to form a 3- to 10 membered heterocyclic or 5- to 10-membered heteroaryl each optionally substituted with one or more substituents independently selected from the group consisting of halo, —$C_1$-$C_{12}$ alkyl, —$C_2$-$C_{12}$ alkenyl, —$C_2$-$C_{12}$ alkynyl, OH, $OR_x$, $NH_2$, $NHR_x$, $N(R_x)_2$, $C(O)NH_2$, $C(O)N(R_x)_2$, oxo, halo-$C_1$-$Cl_2$ alkyl, $C_1$-$C_{12}$ alkyl substituted with OH or $OR_x$, 5- to 10-membered heteroaryl, 3- to 10-membered heterocyclic, $SO_2H$, and $SO_2(C_1$-$C_{12}$ alkyl); wherein $R_x$ is $C_1$-$C_{12}$ alkyl;

E is $CH_2$;

each of $J_1$, $J_2$, $J_3$ and $J_4$ is independently $CH_2$; and m and n are each independently selected from the group consisting of 0, 1, 2 and 3.

2. The compound of claim 1 or a pharmaceutically acceptable salt, thereof; having the Formula (Ib):

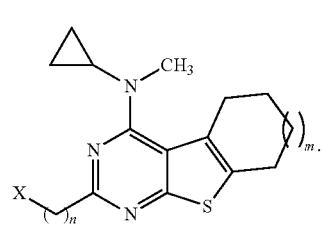

3. The compound of claim 2, wherein X is $C(O)R_3$, $C(O)OR_3$, $C(O)NR_aR_b$, $C(O)NR_aS(O)_2R_3$, $S(O)_2NR_aR_b$, or $OR_3$; or a pharmaceutically acceptable salt thereof.

4. The compound of claim 3, wherein X is $C(O)R_3$ and $R_3$ is $C_1$-$C_{10}$ alkyl optionally substituted with one or more substituents selected from the group consisting of halo, OH and $OR_x$, wherein $R_x$ is $C_1$-$C_{12}$ alkyl; or a pharmaceutically acceptable salt thereof.

5. The compound of claim 3, wherein X is $C(O)NR_aR_b$ and $R_a$ and $R_b$ are each independently hydrogen or $C_1$-$C_{10}$ alkyl optionally substituted with one or more substituents independently selected from halo, —$C_1$-$C_{12}$ alkyl, —$C_2$-$C_{12}$ alkenyl, —$C_2$-$C_{12}$ alkynyl, OH, $OR_x$, $NH_2$, $NHR_x$, $N(R_x)_2$, $C(O)NH_2$, $C(O)N(R_x)_2$, oxo, halo-$C_1$-$Cl_2$ alkyl, $C_1$-$C_{12}$ alkyl substituted with OH or $OR_x$, 5- to 10-membered heteroaryl, 3- to 10-membered heterocyclic, $SO_2H$, and $SO_2(C_1$-$C_{12}$ alkyl); wherein $R_x$ is $C_1$-$C_{12}$ alkyl, or wherein $R_a$ and $R_b$ are taken together with the nitrogen atom to which they are attached to form 3- to 10-membered heterocyclic or 5- to 10-membered heteroaryl, each optionally substituted with one or more substituents independently selected from halo, —$C_1$-$C_{12}$ alkyl, —$C_2$-$C_{12}$ alkenyl, —$C_2$-$C_{12}$ alkynyl, OH, $OR_x$, $NH_2$, $NHR_x$, $N(R_x)_2$, $C(O)NH_2$, $C(O)N(R_x)_2$, oxo, halo-$C_1$-$Cl_2$ alkyl, $C_1$-$C_{12}$ alkyl substituted with OH or $OR_x$, 5- to 10-membered heteroaryl, 3- to 10-membered heterocyclic, $SO_2H$, and $SO_2(C_1$-$C_{12}$ alkyl); wherein $R_x$ is $C_1$-$C_{12}$ alkyl; or a pharmaceutically acceptable salt thereof.

6. The compound of claim 3, wherein X is $OR_3$ and $R_3$ $C_1$-$C_{10}$ alkyl optionally substituted with halo, OH and $OR_x$, wherein $R_x$ is $C_1$-$C_{12}$ alkyl; or a pharmaceutically acceptable salt thereof.

7. The compound of claim 2, wherein m is 0 or 1; or a pharmaceutically acceptable salt thereof.

8. The compound of claim 2, wherein n is 1; or a pharmaceutically acceptable salt thereof.

9. The compound of claim 2, wherein the compound is selected from the group consisting of:

2-(4-(cyclopropyl(methyl)amino)-5,6,7,8-tetrahydrobenzo[4,5]thieno[2,3-d]pyrimidin-2-yl)-N-methylacetamide, 2-(4-(cyclopropyl(methyl)amino)-5,6,7,8-tetrahydrobenzo[4,5]thieno[2,3-d]pyrimidin-2-yl) acetic acid, 2-(4-(cyclopropyl(methyl)amino)-5,6,7,8-tetrahydrobenzo[4,5]thieno[2,3-d]pyrimidin-2-yl)-N,N-dimethylacetamide and Cyclopropyl-(2-methoxymethyl-5,6,7,8-tetrahydro-benzo[4,5]thieno[2,3-d]pyrimidin-4-yl)-methyl-amine.

10. A compound selected from the group consisting of those shown in the Table below:

| Compound |
|---|
| 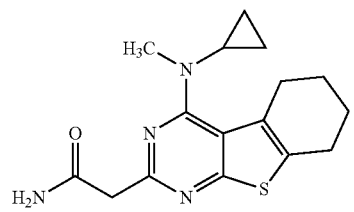 [SMILES: CN(c1nc(CC(N)=O)nc2sc3c(c12)CCCC3)C1CC1]<br>2-(4-(Cyclopropyl(methyl)amino)-5,6,7,8-tetrahydrobenzo[4,5]thieno[2,3-d]pyrimidin-2-yl)acetamide |
| 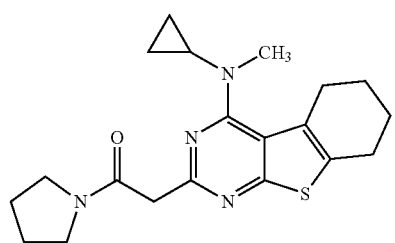 [SMILES: CN(c1nc(CC(=O)N2CCCC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-pyrrolidin-1-yl-ethanone- |
| 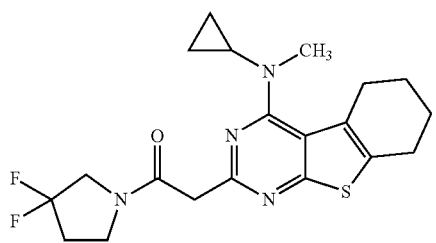<br>2-[4-(Cyclopropyl-methyl-amino)-5,6,7,8-tetrahydro-benzo[4,5]thieno[2,3-d]pyrimidin-2-yl]-1-(3,3-difluoro-pyrrolidin-1-yl)-ethanone |
| 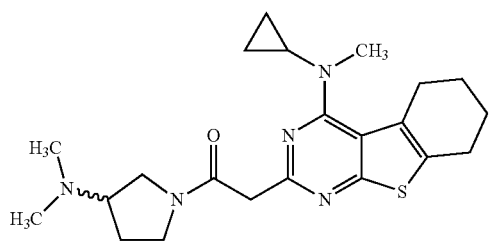 [SMILES: CN(C)C1CCN(C(=O)Cc2nc(N(C)C3CC3)c3c4c(sc3n2)CCCC4)C1]<br>2-[4-(Cyclopropyl-methyl-amino)-5,6,7,8-tetrahydro-benzo[4,5]thieno[2,3-d]pyrimidin-2-yl]-1-(3-dimethylamino-pyrrolidin-1-yl)-ethanone |

-continued

| Compound |
|---|
| 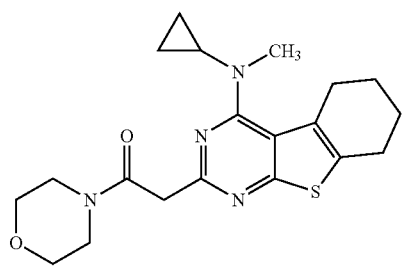 [SMILES: CN(c1nc(CC(=O)N2CCOCC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-morpholin-4-yl-ethanone |
| 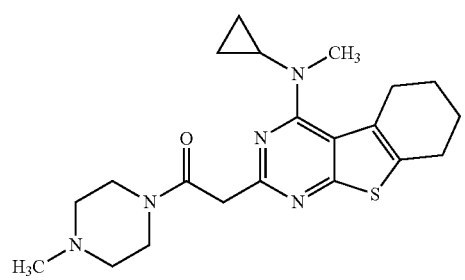 [SMILES: CN1CCN(C(=O)Cc2nc(N(C)C3CC3)c3c4c(sc3n2)CCCC4)CC1]<br>2-[4-(Cyclopropyl-methyl-amino)-5,6,7,8-tetrahydro-benzo[4,5]thieno[2,3-d]pyrimidin-2-yl]-1-(4-methyl-piperazin-1-yl)-ethanone |
| 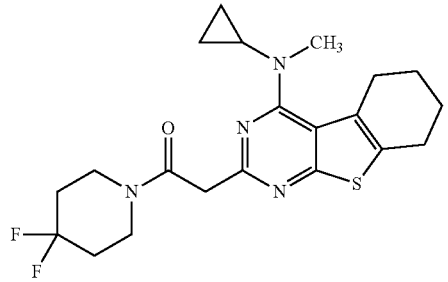 [SMILES: CN(c1nc(CC(=O)N2CCC(F)(F)CC2)nc2sc3c(c12)CCCC3)C1CC1]<br>2-[4-(Cyclopropyl-methyl-amino)-5,6,7,8-tetrahydro-benzo[4,5]thieno[2,3-d]pyrimidin-2-yl]-1-(4,4-difluoro-piperidin-1-yl)-ethanone |
| 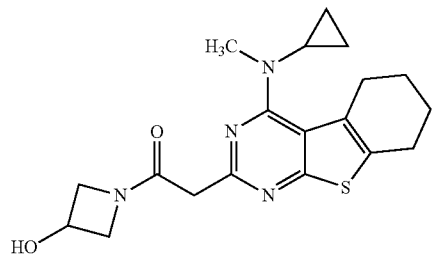 [SMILES: CN(c1nc(CC(=O)N2CC(O)C2)nc2sc3c(c12)CCCC3)C1CC1]<br>2-(4-(Cyclopropyl(methyl)amino)-5,6,7,8-tetrahydrobenzo[4,5]thieno[2,3-d]pyrimidin-2-yl)-1-(3-hydroxyazetidin-1-yl)ethanone |

| Compound |
|---|
| 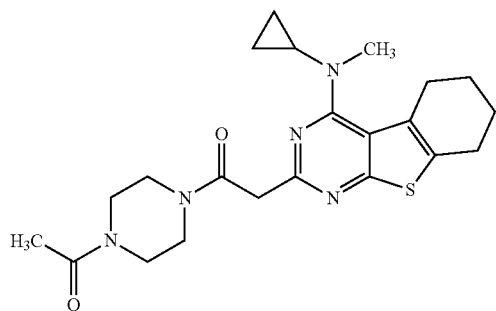 [SMILES: CC(=O)N1CCN(C(=O)Cc2nc(N(C)C3CC3)c3c4c(sc3n2)CCCC4)CC1] 1-(4-Acetyl-piperazin-1-yl)-2-[4-(Cyclopropyl-methyl-amino)-5,6,7,8-tetrahydro-[1]benzothieno[2,3-d]pyrimidin-2-yl]-ethanone |
| 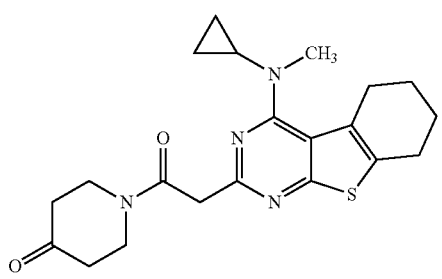 [SMILES: CN(c1nc(CC(=O)N2CCC(=O)CC2)nc2sc3c(c12)CCCC3)C1CC1] 1-{2-[4-(Cyclopropyl-methyl-amino)-5,6,7,8-tetrahydro-benzo[4,5]thieno[2,3-d]pyrimidin-2-yl]-acetyl}-piperidin-4-one |
| 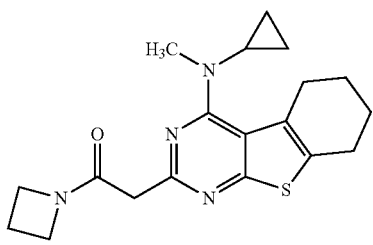 [SMILES: CN(c1nc(CC(=O)N2CCC2)nc2sc3c(c12)CCCC3)C1CC1] 1-(Azetidin-1-yl)-2-(4-(cyclopropyl(methyl)amino)-5,6,7,8-tetrahydrobenzo[4,5]thieno[2,3-d]pyrimidin-2-yl)ethanone |
| 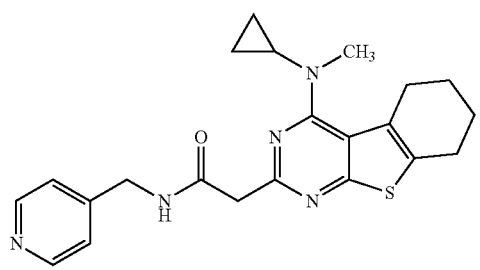 [SMILES: CN(c1nc(CC(=O)NCc2ccncc2)nc2sc3c(c12)CCCC3)C1CC1] 2-[4-(Cyclopropyl-methyl amino)-5,6,7,8-Tetrahydrobenzo(4,5)thieno(2,3-d)pyrimidin]-N-yridin-4-ylmethyl)-acetamide |

| Compound |
|---|
| 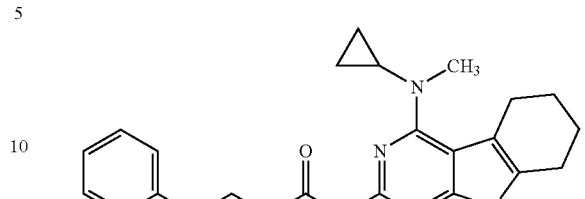 2-[4-(Cyclopropyl-methylamino)-5,6,7,8-tetrahydrobenzo(4,5)thieno(2,3-d)pyrimidin]-pyrimidin-2-yl]-N-(2-pyridin-2-yl-ethyl)-acetamide |
| 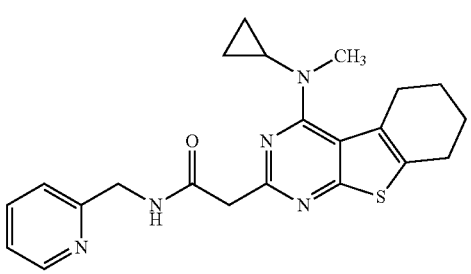 [SMILES: CN(c1nc(CC(=O)NCc2ccccn2)nc2sc3c(c12)CCCC3)C1CC1] 2-[4-(Cyclopropyl-methyl amino)-5,6,7,8-tetrahydrobenzo(4,5)thieno(2,3-d)pyrimidin]-pyrimidin-2-yl]-N-pyridin-2-yl-methylacetamide |
| 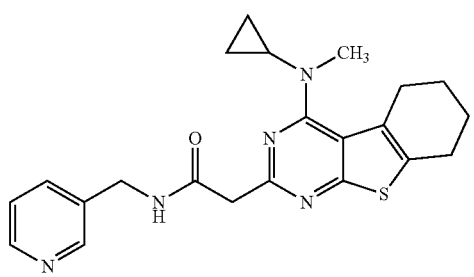 [SMILES: CN(c1nc(CC(=O)NCc2cccnc2)nc2sc3c(c12)CCCC3)C1CC1] 2-(4-(Cyclopropyl-methyl amino)-5,6,7,8-tetrahydrobenzo(4,5)thieno(2,3-d)pyrimidin)-N-yridin-2-ylmethyl)-acetamide |
| 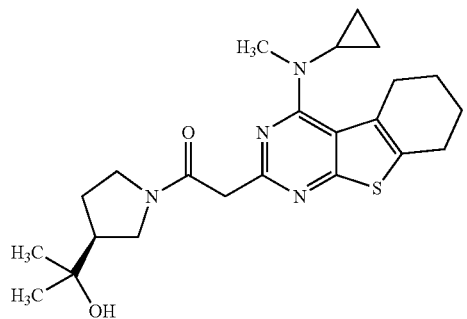 [SMILES: CN(c1nc(CC(=O)N2CC[C@H](C(C)(C)O)C2)nc2sc3c(c12)CCCC3)C1CC1] (S)-2-(4-(Cyclopropyl(methyl)amino)-5,6,7,8-tetrahydrobenzo[4,5]thieno[2,3-d]pyrimidin-2-yl)-1-(3-(2-hydroxypropan-2-yl)pyrrolidin-1-yl)ethanone |

| 73 -continued | 74 -continued |
|---|---|
| Compound | Compound |

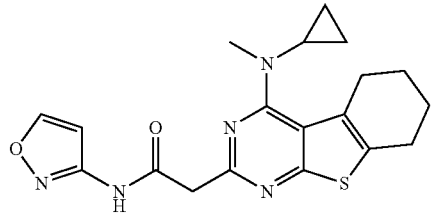 [SMILES: CN(c1nc(CC(=O)Nc2ccon2)nc2sc3c(c12)CCCC3)C1CC1]

2-[4-(Cyclopropyl-methyl amino)-5,6,7,8-
tetrahydrobenzo(4,5)thieno(2,3-d)
pyrimidin]-2-yl]-N-(2-pyridin-4-yl-ethyl)-
acetamide

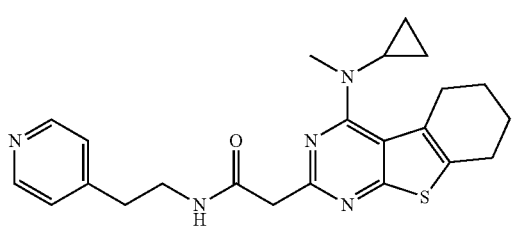 [SMILES: CN(c1nc(CC(=O)NCCc2ccncc2)nc2sc3c(c12)CCCC3)C1CC1]

2-[4-(Cyclopropyl-methyl amino)-5,6,7,8-
tetrahydrobenzo(4,5)thieno(2,3-d)
pyrimidin]-2-yl]-N-(2-pyridin-4-yl-ethyl)-
acetamide

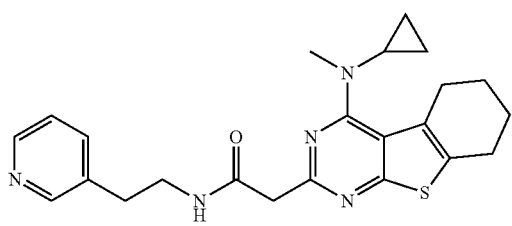

2-[4-(Cyclopropyl-methyl amino)-5,6,7,8-
tetrahydrobenzo(4,5)thieno(2,3-d)
pyrimidin]-pyridin-2-yl]-N-(2-pyridin-3-yl-
ethyl)-acetamide

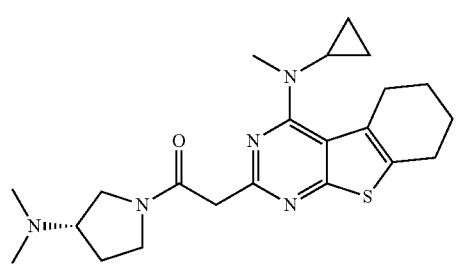 [SMILES: CN(c1nc(CC(=O)N2CC[C@H](N(C)C)C2)nc2sc3c(c12)CCCC3)C1CC1]

2-[4-(Cyclopropyl-methyl-amino)-5,6,7,8-
tetrahydrobenzo[4,5]thieno[2,3-d]pyrimidin-
2yl]-1-((s)-3-dimethylamino-pyrrolidin-1-yl)-
ethanone

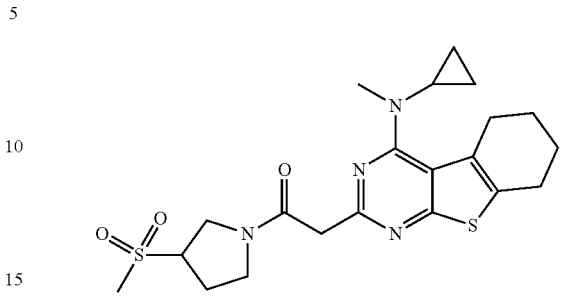

2-[4-(Cyclopropyl-methyl-amino)-5,6,7,8-
tetrahydro-benzo[4,5]thieno[2,3-d]pyrimidin-
2yl]-1-(3-methanesulfonyl-pyrrolidin-1-yl)-
ethanone

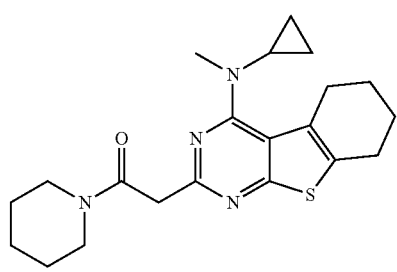 [SMILES: CN(c1nc(CC(=O)N2CCCCC2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2yl]-1-piperidin-1-yl-ethanone

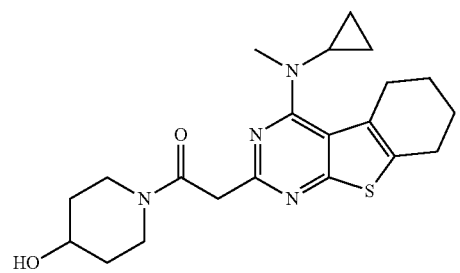 [SMILES: CN(c1nc(CC(=O)N2CCC(O)CC2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl]-1-(4-hydroxy-piperidin-1-yl)-ethanone

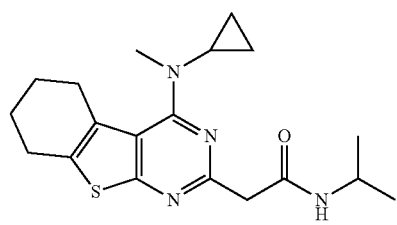 [SMILES: CC(C)NC(=O)Cc1nc(N(C)C2CC2)c2c3c(sc2n1)CCCC3]

2-[4-(Cyclopropyl-methyl-amino)-5,6,7,8-
tetrahydro-benzo[4,5]thieno[2,3-d]pyrimidin-
2-yl]-N-isopropyl-acetamide

| 75 -continued | 76 -continued |
|---|---|
| Compound | Compound |

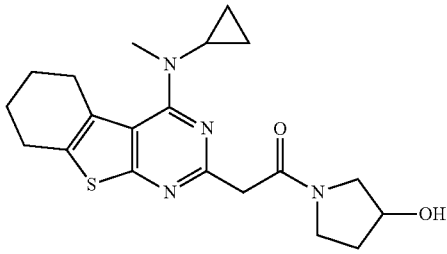 [SMILES: CN(c1nc(CC(=O)N2CCC(O)C2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl]-1-(3-hydroxy-pyrrolidin-1-yl)-ethanone

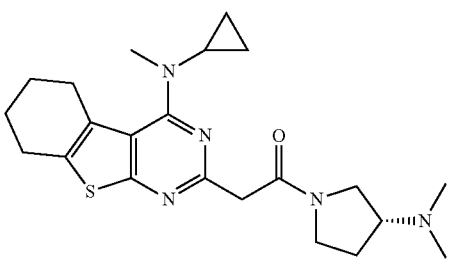 [SMILES: CN(c1nc(CC(=O)N2CC[C@@H](N(C)C)C2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl]-1-((R)-3-dimethylamino-pyrrolidin-1-yl)-
ethanone

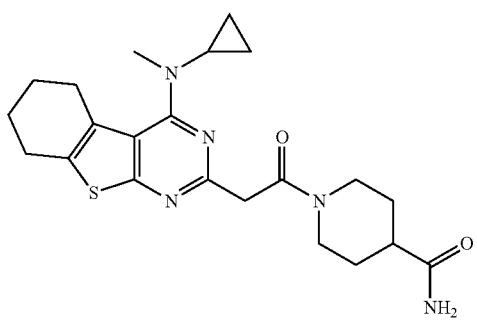 [SMILES: CN(c1nc(CC(=O)N2CCC(C(N)=O)CC2)nc2sc3c(c12)CCCC3)C1CC1]

1-{2-[4-(Cyclopropyl-methyl-amino)-5,6,7,8-
tetrahydro-benzo[4,5]thieno[2,3-d]pyrimidin-
2-yl]-acetyl}-piperidine-4-carboxylic acid
amide

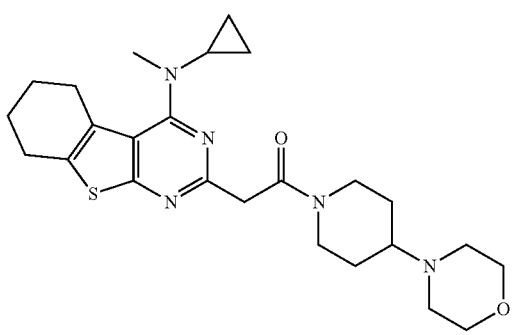 [SMILES: CN(c1nc(CC(=O)N2CCC(N3CCOCC3)CC2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl1-1-(4-morpholin-4-yl-piperidin-1-yl)-
ethanone

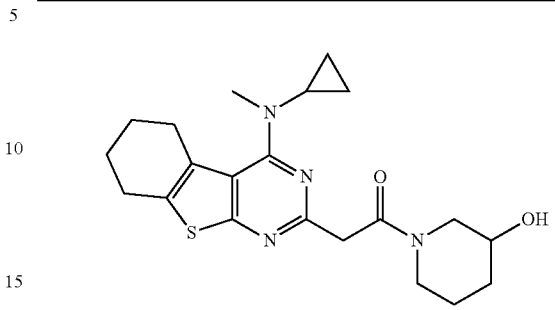

2-[4-(Cyclopropyl-methyl-amino)-5,6,7,8-
tetrahydro-benzo[4,5]thieno[2,3-d]pyrimidin-
2-yl]-1-(3-hydroxy-piperidin-1-yl)-ethanone

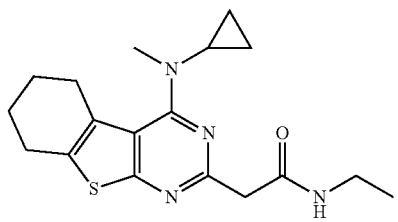 [SMILES: CCNC(=O)Cc1nc(N(C)C2CC2)c2c3c(sc2n1)CCCC3]

2-[4-(Cyclopropyl-methyl-amino)-5,67,8-
tetrahydro-benzo[4,5]thieno[2,3-d]pyrimidin-
2-yl]-N-ethyl-acetamide

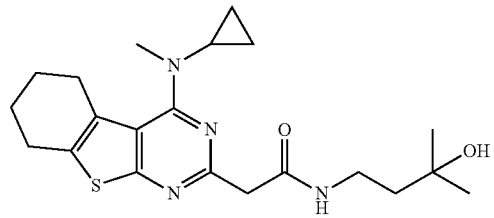 [SMILES: CN(c1nc(CC(=O)NCCC(C)(C)O)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl]-N-(3-hydroxy-3-methyl-butyl)-acetamide

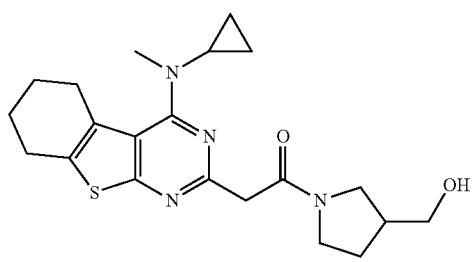 [SMILES: CN(c1nc(CC(=O)N2CCC(CO)C2)nc2sc3c(c12)CCCC3)C1CC1]

2-[4-(Cyclopropyl-methyl-amino)-5,6,7,8-
tetrahydro-benzo[4,5]thieno[2,3-d]pyrimidin-
2-yl]-1-(3-hydroxymethyl-pyrrolidin-1-yl)-
ethanone

| Compound |
|---|
| 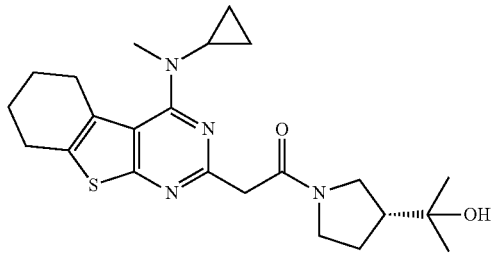 [SMILES: CN(c1nc(CC(=O)N2CC[C@@H](C(C)(C)O)C2)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-[(R)-3-(1-hydroxy-1-methyl-ethyl)-pyrrolidin-1-yl]-ethanone |
| 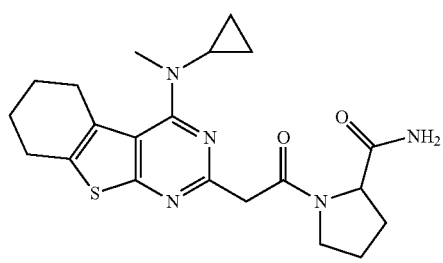 [SMILES: CN(c1nc(CC(=O)N2CCCC2C(N)=O)nc2sc3c(c12)CCCC3)C1CC1]
1-(2-(4-(Cyclopropyl(methyl)amino)-5,6,7,8-tetrahydrobenzo[4,5]thieno[2,3-d]pyrimidin-2-yl)acetyl)pyrrolidine-2-carboxamide |
| 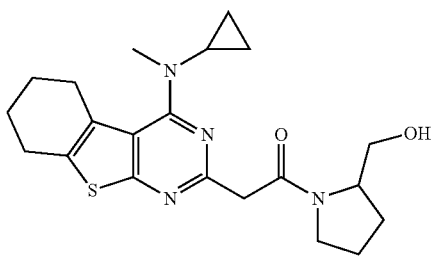 [SMILES: CN(c1nc(CC(=O)N2CCCC2CO)nc2sc3c(c12)CCCC3)C1CC1]
2-[4-(Cyclopropyl-methyl-amino)-5,6,7,8-tetrahydro-benzo[4,5]thieno[2,3-d]pyrimidin-2-yl]-1-(2-hydroxymethyl-pyrrolidin-1-yl)-ethanone |
| 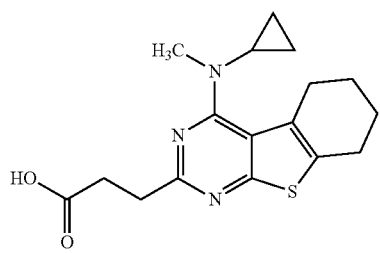 [SMILES: CN(c1nc(CCC(=O)O)nc2sc3c(c12)CCCC3)C1CC1]
3-[4-(Cyclopropyl-methyl-amino)-5,6,7,8-tetrahydro-[1]benzothiopheno[2,3-d]pyrimidin-2-yl]-propionic acid |

| Compound |
|---|
| 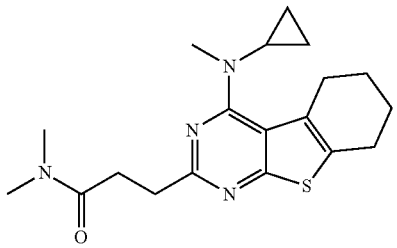 [SMILES: CN(C)C(=O)CCc1nc(N(C)C2CC2)c2c3c(sc2n1)CCCC3]
3-[4-(Cyclopropyl-methyl-amino)-5,6,7,8-tetrahydro-[1]benzothiopheno[2,3-d]pyrimidin-2-yl]-N,N-dimethyl-propionamide |
| 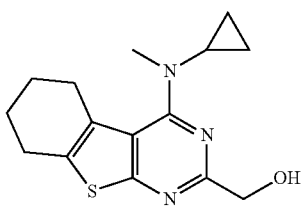 [SMILES: CN(c1nc(CO)nc2sc3c(c12)CCCC3)C1CC1]
[4-(Cyclopropyl-methyl-amino)-5,6,7,8-tetrahydro-benzo[4,5]thieno[2,3-d]pyrimidin-2-yl]-methanol |
| 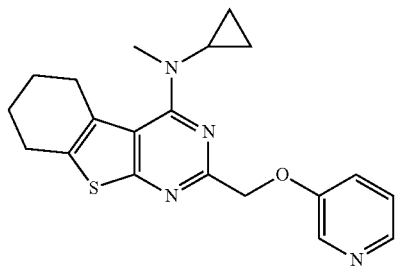 [SMILES: CN(c1nc(COc2cccnc2)nc2sc3c(c12)CCCC3)C1CC1]
Cyclopropyl-methyl-[2-(pyridine-3-yloxymethyl)-5,6,7,8-tetrahydro-benzo[4,5]thieno[2,3-d]pyrimidin-4-yl]-amine |

| Compound |
|---|
| 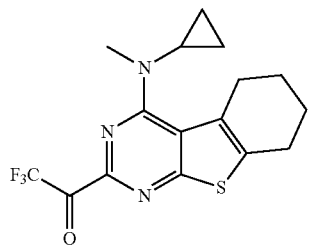 [SMILES: CN(c1nc(C(=O)C(F)(F)F)nc2sc3c(c12)CCCC3)C1CC1]<br>3-[4-(Cyclopropyl-methyl-amino)-5,6,7,8-tetrahydrobenzo[4,5]thieno[2,3-d]pyrimidin-2-yl]-1,1,1-trifluoro-propan-2-one |
| 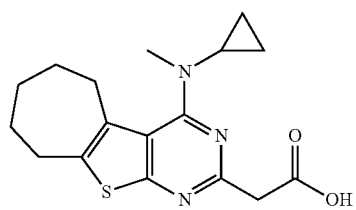 [SMILES: CN(c1nc(CC(=O)O)nc2sc3c(c12)CCCCC3)C1CC1]<br>[4-(Cyclopropyl-methyl-amino)-6,7,8,9-tetrahydro-5H-10-thia-1,3-diazabenz[a]azulen-2-yl]-acetic acid |
| 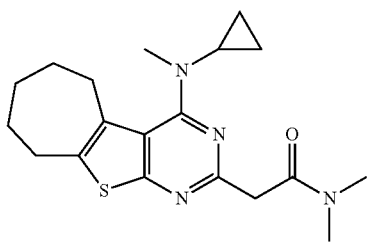 [SMILES: CN(C)C(=O)Cc1nc(N(C)C2CC2)c2c3c(sc2n1)CCCCC3]<br>2-[4-(Cyclopropyl-methyl-amino)-6,7,8,9-tetrahydro-5H-10-thia-1,3-diaza-benz[a]azulen-2-yl]-N,N-dimethyl-acetamide. |

11. A pharmaceutical composition comprising a pharmaceutically acceptable carrier or excipient and a compound of claim 1, or a pharmaceutically acceptable salt thereof.

* * * * *